(12) United States Patent
Simon et al.

(10) Patent No.: US 11,878,996 B2
(45) Date of Patent: *Jan. 23, 2024

(54) SOLID PHASE PEPTIDE SYNTHESIS PROCESSES AND ASSOCIATED SYSTEMS

(71) Applicant: Massachusetts Institute of Technology, Cambridge, MA (US)

(72) Inventors: Mark David Simon, Boston, MA (US); Bradley L. Pentelute, Cambridge, MA (US); Andrea Adamo, Cambridge, MA (US); Patrick Louis Heider, Midland, MI (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 483 days.

This patent is subject to a terminal disclaimer.

(21) Appl. No.: 17/127,951

(22) Filed: Dec. 18, 2020

(65) Prior Publication Data

US 2021/0188899 A1    Jun. 24, 2021

Related U.S. Application Data

(63) Continuation of application No. 15/695,795, filed on Sep. 5, 2017, now Pat. No. 10,988,504, which is a continuation of application No. 14/853,683, filed on Sep. 14, 2015, now Pat. No. 9,868,759, which is a continuation of application No. 13/833,745, filed on Mar. 15, 2013, now Pat. No. 9,169,287.

(51) Int. Cl.
| | |
|---|---|
| *C07K 1/04* | (2006.01) |
| *C07K 1/06* | (2006.01) |
| *C07K 1/08* | (2006.01) |
| *B01J 19/00* | (2006.01) |
| *B01J 8/00* | (2006.01) |

(52) U.S. Cl.
CPC ............ *C07K 1/045* (2013.01); *B01J 8/00* (2013.01); *B01J 19/00* (2013.01); *B01J 19/0053* (2013.01); *C07K 1/04* (2013.01); *C07K 1/042* (2013.01); *C07K 1/061* (2013.01); *C07K 1/08* (2013.01)

(58) Field of Classification Search
CPC .......... C07K 1/045; C07K 1/04; C07K 1/042; C07K 1/061; C07K 1/081; C07K 1/08
See application file for complete search history.

(56) References Cited

U.S. PATENT DOCUMENTS

| | | | |
|---|---|---|---|
| 4,093,550 A | 6/1978 | Stahl et al. | |
| 4,192,796 A | 3/1980 | Mosby et al. | |
| 4,192,798 A | 3/1980 | Verlander et al. | |
| 4,598,049 A | 7/1986 | Zelinka et al. | |
| 4,668,476 A | 5/1987 | Bridgham et al. | |
| 4,746,490 A | 5/1988 | Saneii | |
| 4,816,513 A | 3/1989 | Bridgham et al. | |
| 4,861,866 A | 8/1989 | Durrum et al. | |
| 5,807,525 A | 9/1998 | Allen et al. | |
| 5,861,125 A | 1/1999 | Shively | |
| 6,028,172 A | 2/2000 | Stepaniuk et al. | |
| 6,033,631 A | 3/2000 | Zuckermann et al. | |
| 7,348,404 B2 | 3/2008 | Holm et al. | |
| 7,566,697 B2 | 7/2009 | Botti et al. | |
| 7,902,488 B2 | 3/2011 | Collins et al. | |
| 8,206,593 B2 | 6/2012 | Lee et al. | |
| 8,535,947 B2 | 9/2013 | Menakuru et al. | |
| 8,835,179 B2 | 9/2014 | Chang et al. | |
| 9,169,287 B2 | 10/2015 | Simon et al. | |
| 9,669,380 B2 | 6/2017 | Collins et al. | |
| 9,695,214 B2 | 7/2017 | Simon et al. | |
| 9,868,759 B2 | 1/2018 | Simon et al. | |
| 10,683,325 B2 | 6/2020 | Thomas, III et al. | |
| 10,889,613 B2 | 1/2021 | Simon et al. | |
| 10,988,504 B2 | 4/2021 | Simon et al. | |
| 2014/0275481 A1 | 9/2014 | Simon | |
| 2015/0217254 A1 | 8/2015 | Boroomand | |
| 2015/0217524 A1 | 8/2015 | Rudmann et al. | |
| 2016/0031931 A1 | 2/2016 | Simon et al. | |
| 2016/0102118 A1 | 4/2016 | Simon et al. | |
| 2017/0081358 A1 | 3/2017 | Thomas, III et al. | |
| 2017/0081359 A1 | 3/2017 | Thomas, III et al. | |

(Continued)

FOREIGN PATENT DOCUMENTS

| | | |
|---|---|---|
| CN | 101665528 A | 3/2010 |
| CN | 102924568 A | 2/2013 |

(Continued)

OTHER PUBLICATIONS

[No Author Listed], Peptide Synthesis. Thermo Fisher Scientific. Waltham, MA. Accessed Nov. 16, 2021 by USPTO from <https://www.thermofisher.com/us/en/home/life-science/protein-biology/protein-biology-learning-center/protein-biology-resource-library/pierce-protein-methods/peptide-synthesis.html>. 6 pages.

Denton, What do you do when your peptide synthesis fails? Biotage. Uppsala, Sweden. Accessed from <https://selekt.biotage.com/peptideblogs/what-do-you-do-when-your-peptide-synthesis-fails>. Feb. 14, 2019. 6 pages.

EP 14711046.4, Dec. 3, 2021, Summons to Attend Oral Proceedings.

Summons to Attend Oral Proceedings for European Application No. 14711046.4, mailed Dec. 3, 2021.

(Continued)

*Primary Examiner* — Jeanette M Lieb

(74) *Attorney, Agent, or Firm* — Wolf, Greenfield & Sacks, P.C.

(57) ABSTRACT

Systems and processes for performing solid phase peptide synthesis are generally described. Solid phase peptide synthesis is a known process in which amino acid residues are added to peptides that have been immobilized on a solid support. In certain embodiments, the inventive systems and methods can be used to perform solid phase peptide synthesis quickly while maintaining high yields. Certain embodiments relate to processes and systems that may be used to heat, transport, and/or mix reagents in ways that reduce the amount of time required to perform solid phase peptide synthesis.

12 Claims, 24 Drawing Sheets

Specification includes a Sequence Listing.

(56) References Cited

U.S. PATENT DOCUMENTS

| | | |
|---|---|---|
| 2018/0057525 A1 | 3/2018 | Simon et al. |
| 2018/0066012 A1 | 3/2018 | Simon et al. |
| 2021/0047365 A1 | 2/2021 | Thomas et al. |
| 2021/0188900 A1 | 6/2021 | Simon et al. |
| 2021/0188901 A1 | 6/2021 | Thomas, III et al. |

FOREIGN PATENT DOCUMENTS

| | | | |
|---|---|---|---|
| EP | 0156588 | A2 | 10/1985 |
| EP | 1923396 | A2 | 5/2008 |
| JP | 60-237097 | A | 11/1985 |
| JP | 2000-511934 | A | 9/2000 |
| JP | 2001-527544 | A | 12/2001 |
| JP | 2005-015483 | A | 1/2005 |
| JP | 2005-529188 | A | 9/2005 |
| JP | 2008-110977 | A | 5/2008 |
| JP | 2002-533299 | A | 9/2009 |
| KR | 10-1014799 | B1 | 2/2011 |
| WO | WO 82/03077 | A1 | 9/1982 |
| WO | WO 85/01224 | A1 | 3/1985 |
| WO | WO 98/34633 | A1 | 8/1998 |
| WO | WO 00/18790 | A1 | 4/2000 |

OTHER PUBLICATIONS

JP2021-083136, Feb. 6, 2023, Notice of Reasons for Rejection.
Japanese Notice of Reasons for Rejection dated Feb. 6, 2023, for JP Application No. 2021-083136.
U.S. Appl. No. 17/558,525, filed Dec. 21, 2021, Simon et al.
U.S. Appl. No. 17/747,952, filed May 18, 2022, Thomas et al.
Partial European Search Report dated Feb. 12, 2020 for Application No. EP 19202972.6.
Extended European Search Report dated Jun. 24, 2020 for Application No. EP 19202972.6.
European Office Action dated Aug. 21, 2020 for EP Application No. EP 14711046.4.
Japanese Office Action dated Jan. 25, 2021 for Application No. JP 2018-197185.
Extended European Search Report dated Apr. 12, 2019 for Application No. EP 16847410.4.
Invitation to Pay Additional Fees dated Jun. 17, 2014 for PCT/US2014/017970.
International Search Report and Written Opinion for PCT/US2014/017970 dated Sep. 22, 2014.
International Preliminary Report on Patentability for PCT/US2014/017970 dated Sep. 24, 2015.
International Search Report and Written Opinion for PCT/US2016/052179 dated Dec. 2, 2016.
International Preliminary Report on Patentability dated Mar. 29, 2018 for Application No. PCT/US2016/052179.
[No Author Listed] Focus XC: Automated peptide synthesizer. Advanced Automated Peptide Protein Technologies. Product Description. 2006. Louisville, KY. 4 pages.
[No Author Listed], Apogee: Totally automated single peptide synthesizer. Advanced Automated Peptide Protein Technologies. Product Description. 2006. Louisville, KY. 4 pages.
[No Author Listed], Applied Biosystems User Bulletin No. 35: Model 431A Peptide Synthesizer. Nov. 1993. 26 pages. updated Jul. 2002.
[No Author Listed], Bachem: The Bachem Practice of SPPS. Edition 2005. 84 pages.
[No Author Listed], CS Bio Specifications for CS336X. Last Accessed Jun. 20, 2016.; http://www.csbio.com/peptide-synthesizers/cs-336x. 2 pages.
[No Author Listed], Endeavor 90: Tabletop peptide synthesizer. Advanced Automated Peptide Protein Technologies. Product Description. 2006. Louisville, KY. 4 pages.
[No Author Listed], Liberty 1: Advantages. CEM Corporation. 2011. Last accessed online at <http://www.cem.com/liberty-1-advantages.html> on May 9, 2013. 2 pages.
[No Author Listed], Liberty Blue. Microwave Peptide Synthesizer: peptide synthesis made fast and efficient. CEM Sales Literature LibBlue B105, accessible via: www.brs.be/pdf/525_broch_libblue_b105.pdf; dated Feb. 18, 2010. 9 pages.
[No Author Listed], Liberty. Microwave Peptide Synthesis. CEM Sales Literature Liberty, accessible via: www.cem.hu/pdf/liberty_eng.pdf; dated Mar. 6, 2005. 3 pages.
[No Author Listed], Liberty: Advantages. CEM Corporation. 2011. Last accessed online at <http://www.cem.com/liberty-advantages.html> on May 9, 2013. 3 pages.
[No Author Listed], Liberty: Liberty Overview. CEM Corporation. 2011. Last accessed online at <http://www.cem.com/liberty.html> on May 9, 2013. 2 pages.
[No Author Listed], PL-Wang Resin, Sales Literature, accessible via: www.cypress-international.com/imagepolymerlabs/wang.pdf; dated Apr. 27, 2003. 3 pages.
[No Author Listed], Pseudoproline Dipeptides, Corden Pharm Switzerland, Sales Literature, 2011. 4 pages.
[No Author Listed], Pub Chem Compound Summary for CID: 8083, Morpholine. https://pubchem.ncbi.nlm.nih.gov/compound/8083#section=Chemical-and-Physical-Properties. 2018. 98 pages.
[No Author Listed], Static Mixing, Reaction, Heat Transfer & Fluid Dynamics Technology. Stamixco Technical Bulletin. Jul. 18, 2007. 8 pages.
[No Author Listed], Synthesis of Crosslinked Polymers, Chapter 4, Results and Discussion, Jun. 18, 2010, available online at: http://shodhganga.inflibnet.ac.in/bitstream/10603/146/11/11_chapter4.pdf. 102 pages.
[No Author Listed], We Have the Art of Peptide Synthesis Down to a Science. 2010. CEM Corporation. Complete Peptide Brochure. 9 pages.
Adamo et al., On-demand continuous-flow production of pharmaceuticals in a compact, reconfigurable system. Science. Apr. 1, 2016;352(6281):61-7. doi: 10.1126/science.aaf1337.
Al-Warhi, Recent development in peptide coupling reagents. J Saudi Chem Soc. 2012;16:97-116. Epub Jan. 5, 2011.
Bacsa et al., Rapid solid-phase synthesis of a calmodulin-binding peptide using controlled microwave irradiation. Nature Protocols. 2007; 2(9):2222-2227.
Basca et al., Rapid solid-phase peptide synthesis using thermal and controlled microwave irradiation. J Pept Sci. Oct. 2006;12(10):633-8.
Bayer et al., Polystyrene-immobilized PEG chains: Dynamics and application in peptide synthesis, immunology, and chromatography. Ch. 20. In: Harris, J.M. (eds). Poly(Ethylene Glycol) Chemistry. Biotechnical and biomedical applications. Springer,Boston. 1992;325-45.
Carpino et al., Synthesis of "Difficult" Peptide Sequences : Application of a Depsipeptide Technique to the Jung-Redemann 10- and 26-mers and the Amyloid Peptide Abeta(1-42). Tetrahedron Lett. 2004;45:7519-23.
Carter et al., ReactIR Flow Cell: A New Analytical Tool for Continuous Flow Chemical Processing. Org Process Res Dev. 2010;14(2):393-404.
Cen et al., Progress on synthesis of peptide by microwave irradiation. Chemical World. Jul. 2009;Jul. 2009:439-42.
Coin et al., Solid-phase peptide synthesis: from standard procedures to the synthesis of difficult sequences. Nat Protoc. 2007;2(12):3247-56.
Collins et al., High-efficiency solid phase peptide synthesis (HE-SPPS). Organic Letters. Jan. 23, 2014; 16:940-943.
Collins et al., Microwave energy: a versatile tool for the biosciences. Org Biomol Chem. 2007; 5:1141-1150.
Dang et al., Enhanced Solvation of Peptides Attached to "Solid-Phase" Resins: Straightforward Syntheses of the Elastin Sequence Pro-Gly-Val-Gly-Val-Pro-Gly-Val-Gly-Val. Org Lett. Jul. 17, 2015;17(14):3521-3. doi: 10.1021/acs.orglett.5b01632. Epub Jun. 25, 2015.
Dettin et al., SPPS of difficult sequences. J Peptide Res. 1997;49:103-11.

(56) References Cited

OTHER PUBLICATIONS

Dryland et al., Peptide synthesis. Part 11. A system for continuous flow solid phase peptide synthesis using fluorenylmethoxycarbonyl-amino acid pentafluorophenyl esters. Tetrahedron. 198;44(3):859-76.
Dryland et al., Peptide synthesis. Part 8. A system for solid-phase synthesis under low pressure continuous flow conditions. J Chem Soc, Perkin Trans 1. Jan. 1, 1986:125-37.
Finneman et al., Novel approach for optimization of a 'difficult' peptide synthesis by utilizing quantitative reaction monitoring assays. J Pept Sci. 2012; 18:511-8. Epub Jul. 4, 2012.
Fuentes et al., Fast conventional synthesis of 65-74ACP on the Symphony® and Prelude™. Protein Technologies, Inc. Tuscon, AZ. 1 page. 2006.
Goodman et al., Synthesis of Peptides and Peptidomimetics. New York: Thieme Stuttgart.; 2004; vol. E22a; Section 2.1 Amino Group. p. 65.
Goodman et al., Synthesis of Peptides and Peptidomimetics. New York: Thieme Stuttgart.; 2004; vol. E22b; Section 5.3 Examples of Protein Synthesis on Solid Support. p. 65.
Goodman et al., Synthesis of Peptides and Peptidomimetics. New York: Thieme Stuttgart.; 2004; vol. E22c; Section 9.2 Synthesis of Peptides Containing Proline Analogues. p. 65.
Gude et al., An accurate method for the quantitation of Fmoc-derivatized solid phase supports. Letters in Peptide Science; 2002; 9(4): 203-206.
Han et al., Occurrence and minimization of cysteine racemization during stepwise solid-phase peptide synthesis 1, 2. J Org Chem. Jul. 1997;62(13):4307-12.
Hjorringgaard et al., Evaluation of COMU as a coupling reagent for in situ neutralization Boc solid phase peptide synthesis. J Pept Sci. Mar. 2012;18(3):199-207. doi: 10.1002/psc.1438. Epub Jan. 17, 2012.
Hood et al., Fast conventional Fmoc solid-phase peptide synthesis with HCTU. J Pept Sci. Jan. 2008;14(1):97-101. Published online Sep. 24, 2007 in Wiley InterScience.
Johnson et al., A reversible protecting group for the amide bond in peptides. Use in the synthesis of 'difficult sequences'. J Chem Soc Chem Commun. 1993;29(4):369-72.
Kaiser et al., Color test for detection of free terminal amino groups in the solid-phase synthesis of peptides. Anal Biochem. Apr. 1970;34(2):595-8.
Kent, Chemical synthesis of peptides and proteins. Annu Rev Biochem. 1988:57-:957-89.
Krchnak et al., Continuous-flow solid-phase peptide synthesis. Tetrahedron Letters. 1987;28(38):4469-4472.
Latassa et al., Abstract: AKTA™ oligopilot™ for Automated Solid Phase Peptide Synthesis. LONZA. Poster presented at the 30th European Peptide Symposium in Helsinki, Finlandia Hall. Aug. 31, 2008:132-3.
Latassa et al., AKTA™ oligopilot™ for Automated Solid Phase Peptide Synthesis. LONZA. Poster presented at the 30th European Peptide Symposium in Helsinki, Finlandia Hall. Aug. 31, 2008. 1 page.
Lukas et al., Solid-phase peptide synthesis under continuous-flow conditions. Proc Natl Acad Sci U S A. May 1981;78(5):2791-5.
McQuade et al., Applying flow chemistry: methods, materials, and multistep synthesis. J Org Chem. Jul. 5, 2013;78(13):6384-9. doi: 10.1021/jo400583m. Epub Jun. 10, 2013.
Meldal et al., Pega: A flow stable polyethylene glycol dimethyl acrylamide copolymer for solid phase synthesis. Tetrahedron Letters. May 19, 1992;33(21):3077-80.
Merrifield et al., Solid Phase Peptide Synthesis I. The Synthesis of a Tetrapeptide. J Am Chem Soc. Jul. 20, 1963; 85:2149-54.
Miralles et al., A review of heating and temperature control in microfluidic systems: techniques and applications. Diagnostics. 2013;3:33-67. doi: 10.3390/diagnostics3010033.
Miranda et al., Accelerated chemical synthesis of peptides and small proteins. Proc Natl Acad Sci U S A. Feb. 16, 1999;96(4):1181-6.

Mong et al., Rapid total synthesis of DARPin pE59 and barnase. Chembiochem. Mar. 2014; 21;15(5):721-33. doi: 10.1002/cbic.201300797. Epub Mar. 11, 2014.
Mäde et al., Automated solid-phase peptide synthesis to obtain therapeutic peptides. Beilstein J Org Chem. May 22, 2014;10:1197-212. doi: 10.3762/bjoc.10.118.
Pedersen et al., Microwave heating in solid-phase peptide synthesis. Chem Soc Rev. 2012;41:1826-44. Published online Oct. 20, 2011 on http://pubs.rsc.org.
Quade, Solid Phase Peptide Synthesis, Strategies and Resins, modified on May 28, 2006, available online at: http://wwwoc. chemie. uni-regensburg.de/OCP/ch/chv/oc22/script/006.pdf. 12 pages.
Quibell et al., Preparation and purification of beta-Amyloid (1-43) via soluble, amide backbone protected intermediates. J Org Chem. Mar. 1994;59(7):1745-50.
Razzaq et al., Continuous-flow microreactor chemistry under high-temperature/pressure conditions. Eur J Org Chem. 2009;2009(9):1321-5.
Reid et al., Automated solid-phase peptide synthesis: use of 2-(1H-benzotriazol-1-yl)-1,1,3,3-tetramethyluronium tetrafluoroborate for coupling of tert-butyloxycarbonyl amino acids. Anal Biochem. Feb. 1, 1992;200(2):301-9.
Sabatino et al., Abstract: Advances in automatic, manual and microwave-assisted solid-phase peptide synthesis. Curr Opin Discov Devel. Nov. 2008;11(6). 1 page.
Sarin et al., Quantitative monitoring of solid-phase peptide synthesis by the ninhydrin reaction. Anal Biochem. Oct. 1981;117(1):147-57.
Schnölzer et al., In situ neutralization in boc-chemistry solid phase peptide synthesis. International Journal of Peptide Research and Therapeutics. 1992;40:180-193. Published online Jun. 2007.
Simon et al., Rapid flow-based peptide synthesis. Chembiochem. Mar. 21, 2014;15(5):713-20. doi:10.1002/cbic.201300796. Epub Mar. 11, 2014.
Sucholeiki et al., New developments in solid phase synthesis supports. Mol Div. Jan. 1, 1998;4:25-30.
Tedebark et al., AKTA™ oligopilot™ for Automated Solid Phase Peptide Synthesis. Proceedings of the 30th European Peptide Symposium in Helsinki, Finlandia Hall. Aug. 10, 2010:450-1.
Varanda et al., Solid-phase peptide synthesis at elevated temperatures: a search for and optimized synthesis condition of unsulfated cholecystokinin-12. J Pept Res. Aug. 1997;50(2):102-8.
Wang et al., Temperature effects on reaction rates for solid phase peptide synthesis. Chem Engin Sci. Jan. 29, 1991; 46(9):2373-6.
Wohr et al., Pseudo-prolines in peptide synthesis: Direct insertion of serine and threonine derived oxazolidines in dipeptides. Tetrahedron Lett. May 29, 1995;36(22):3847-8.
Wu, Biochemistry, China Medical Science Press, Jan. 2010. 6 pages.
Chinese Office Action dated Jul. 8, 2023, for CN Application No. 201911125162.7.
Office Action dated Jun. 2, 2023, for U.S. Appl. No. 17/558,525.
[No Author Listed], Solid phase peptide synthesis (SPPS). 2013. Accessed May 25, 2023 from <https://www.biosyn.com/tew/solid-phase-peptide-synthesis.aspx>. 6 pages.
Glaser, Strategies for optimizing peptide synthesis. Genetic Eng & Biotech News. 2011. Accessed May 25, 2023 from <https://www.genengnews.com/insights/strategies-for-optimizing-peptide-synthesis/>. 13 pages.
Hayashi et al., An efficient approach to synthesize multiple peptides with carboxyl C-termini. Adv Exp Med Biol. 2009;611:177-8.
Chinese Office Action dated Nov. 2, 2022, for CN Application No. 201911125162.7.
Japanese Notice of Reasons for Rejection dated Oct. 19, 2022, for JP Application No. 2018-197185.
Indian Office Action dated Dec. 12, 2019 for Application No. IN 9113/DELNP/2015.
Japanese Office Action dated Mar. 10, 2020 for Application No. JP 2018-197185.
Bacsa et al., Solid-phase synthesis of difficult peptide sequences at elevated temperatures: a critical comparison of microwave and conventional heating technologies. J Org Chem. Oct. 3, 2008;73(19):7532-42. doi: 10.1021/jo8013897. Epub Aug. 27, 2008.

(56) References Cited

OTHER PUBLICATIONS

Fuse et al., Efficient amide bond formation through a rapid and strong activation of carboxylic acids in a microflow reactor. Angew Chem Int Ed. 2014;53:851-5.
Yoshida et al., Flash chemistry: flow chemistry that cannot be done in batch. Chem Commun (Camb). Nov. 4, 2013;49(85):9896-904. doi: 10.1039/c3cc44709j. Epub Aug. 29, 2013.
Yu et al., Enhanced coupling efficiency in solid-phase peptide synthesis by microwave irradiation. J Org Chem. Aug. 1, 1992;57(18):4781-4.
U.S. Appl. No. 17/086,196, filed Oct. 30, 2020, Thomas et al.
U.S. Appl. No. 17/127,961, filed Dec. 18, 2020, Simon et al.
IN 9113/DELNP/2015, Dec. 12, 2019, Indian Office Action.
JP 2018-197185, Mar. 10, 2020, Japanese Office Action.
CN 201911125162.7, Nov. 2, 2022, Chinese Office Action.
JP 2018-197185, Oct. 19, 2022, Japanese Notice of Reasons for Rejection.
Japanese Final Rejection and Denial of Entry of Amendment dated Aug. 31, 2023, for Application No. JP2021-83136.

PnIA(A10L) Conotoxin GCCSLPPCALNNPDYC-CONH$_2$ $[M+2H]^{2+}$ 834.83
$[M+H]^+$ 1668.66

Obs. 1667.66 Da
Calc. 1667.65 Da

FIG. 5A

HIV-1 PR (81-99) PVNIIGRNLLTQIGCTLNF-CONH$_2$ $[M+3H]^{3+}$ 696.06
$[M+2H]^{2+}$ 1043.59

Obs. 2085.17 Da
Calc. 2085.15 Da

FIG. 5B

SOLID PHASE PEPTIDE SYNTHESIS PROCESSES AND ASSOCIATED SYSTEMS

RELATED APPLICATIONS

This application is a continuation of U.S. patent application Ser. No. 15/695,795, filed Sep. 5, 2017, and entitled "Solid Phase Peptide Synthesis Processes and Associated Systems," which is a continuation of U.S. patent application Ser. No. 14/853,683, filed Sep. 14, 2015, and entitled "Solid Phase Peptide Synthesis Processes and Associated Systems," which is a continuation of U.S. application Ser. No. 13/833,745, filed Mar. 15, 2013, and entitled "Solid Phase Peptide Synthesis Processes and Associated Systems," each of which is incorporated herein by reference in its entirety.

TECHNICAL FIELD

Systems and processes for performing solid phase peptide synthesis are generally described.

BACKGROUND

Solid phase peptide synthesis is a process used to chemically synthesize peptides on solid supports. In solid phase peptide synthesis, an amino acid or peptide is bound, usually via the C-terminus, to a solid support. New amino acids are added to the bound amino acid or peptide via coupling reactions. Due to the possibility of unintended reactions, protection groups are typically used. To date, solid phase peptide synthesis has become standard practice for chemical peptide synthesis. The broad utility of solid phase peptide synthesis has been demonstrated by the commercial success of automated solid phase peptide synthesizers. Though solid phase peptide synthesis has been used for over 30 years, fast synthesis techniques have not yet been developed. Accordingly, improved processes and systems are needed.

SUMMARY

Solid phase peptide synthesis processes and associated systems are generally described. Certain embodiments relate to systems and methods which can be used to perform solid phase peptide synthesis quickly while maintaining high yield. In some embodiments, reagents can be heated, transported, and/or mixed in ways that reduce the amount of time required to perform solid phase peptide synthesis. The subject matter of the present invention involves, in some cases, interrelated products, alternative solutions to a particular problem, and/or a plurality of different uses of one or more systems and/or articles.

In some embodiments, a process for adding amino acid residues to peptides is provided. The process comprises, in certain embodiments, providing a plurality of peptides comprising protection groups, each peptide immobilized on a solid support; exposing a deprotection reagent to the immobilized peptides to remove the protection groups from at least a portion of the immobilized peptides; removing at least a portion of the deprotection reagent; exposing activated amino acids to the immobilized peptides such that at least a portion of the activated amino acids are bonded to the immobilized peptides to form newly-bonded amino acid residues; and removing at least a portion of activated amino acids that do not bond to the immobilized peptides. In some embodiments, an amino acid residue is added to at least about 99% of the immobilized peptides during the amino acids exposing step. In certain embodiments, the total amount of time taken to perform the combination of all of the deprotection reagent exposing step, the deprotection reagent removal step, the activated amino acid exposing step, and the activated amino acid removal step is about 10 minutes or less and the protection groups comprise fluorenylmethyloxycarbonyl protection groups and/or the total amount of time taken to perform the combination of all of the deprotection reagent exposing step, the deprotection reagent removal step, the activated amino acid exposing step, and the activated amino acid removal step is about 5 minutes or less.

In certain embodiments, the process comprises flowing a first stream comprising amino acids; flowing a second stream comprising an amino acid activating agent; merging the first and second streams to form a mixed fluid comprising activated amino acids; and within about 30 seconds after merging the first and second streams to form the mixed fluid, exposing the mixed fluid to a plurality of peptides immobilized on a solid support.

In some embodiments, the process comprises heating a stream comprising amino acids such that the temperature of the amino acids is increased by at least about 1° C.; and exposing the heated amino acids to a plurality of peptides immobilized on a solid support, wherein the heating step is performed prior to and within about 30 seconds of exposing the heated amino acids to the peptides.

In certain embodiments, the process comprises providing a plurality of peptides comprising protection groups, each peptide immobilized on a solid support; performing a first amino acid addition cycle comprising exposing amino acids to the immobilized peptides such that an amino acid residue is added to at least about 99% of the immobilized peptides; and performing a second amino acid addition cycle comprising exposing amino acids to the immobilized peptides such that an amino acid residue is added to at least about 99% of the immobilized peptides. In some embodiments, the total amount of time between the ends of the first and second amino acid addition cycles is about 10 minutes or less and the protection groups comprise fluorenylmethyloxycarbonyl protection groups and/or the total amount of time between the ends of the first and second amino acid addition cycles is about 5 minutes or less.

In certain embodiments, the process comprises providing a plurality of peptides immobilized on a solid support; and exposing activated amino acids to the immobilized peptides such that at least a portion of the activated amino acids are bonded to the immobilized peptides to form newly-bonded amino acid residues; wherein an amino acid residue is added to at least about 99% of the immobilized peptides within about 1 minute or less.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 5A is, according to one set of embodiments, a chromatogram and mass spectrum for PnIA (A10L) peptides (SEQ ID NO: 4);

FIG. 5B is, according to one set of embodiments, a chromatogram and mass spectrum for synthesized HIV-1 PR (81-99) peptides (SEQ ID NO: 5);

DETAILED DESCRIPTION

Systems and processes for performing solid phase peptide synthesis are generally described. Solid phase peptide synthesis is a known process in which amino acid residues are added to peptides that have been immobilized on a solid support. In certain embodiments, the inventive systems and methods can be used to perform solid phase peptide synthesis quickly while maintaining high yields. Certain embodiments relate to processes and systems that may be used to heat, transport, and/or mix reagents in ways that reduce the amount of time required to perform solid phase peptide synthesis.

Figure 1:
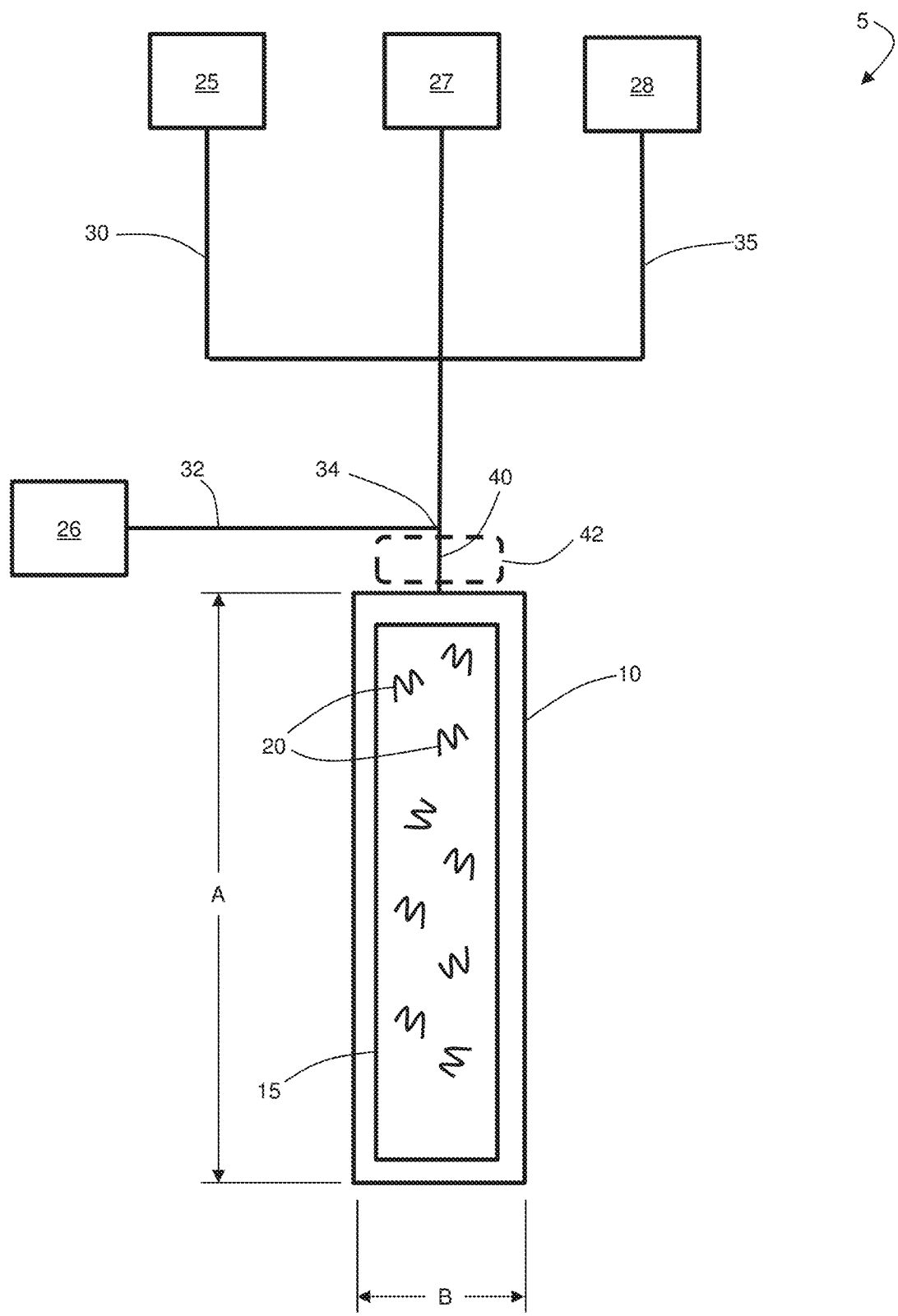
FIG. 1 is a schematic illustration of a system for performing peptide synthesis, according to one set of embodiments.

Certain embodiments relate to a process for adding amino acid(s) to an immobilized peptide. FIG. 1 is a schematic illustration of an exemplary system 5 which can be used to perform certain of the inventive processes described herein. The systems and methods described herein (system 5 in FIG. 1) can, in certain embodiments, involve flow-based synthesis (as opposed to batch-based synthesis, which is employed in many traditional solid phase peptide synthesis systems). In some such embodiments, continuous peptide synthesis can be performed, in which fluid (of one form or another) is substantially continuously transported over the immobilized peptides. For example, reagents and rinsing fluids may be alternatively and continuously transported over the immobilized peptides, in certain embodiments.

In some embodiments, peptides 20 may be immobilized on a solid support 15. Solid support 15 may be contained within a vessel, such as reactor 10. In some embodiments, and as shown in FIG. 1, a plurality of reagent reservoirs may be located upstream of and fluidically connected to reactor 10. In some embodiments, a reagent reservoir 25 contains amino acids (e.g., pre-activated amino acids and/or amino acids that are not fully activated). In some instances, a reagent reservoir 26 contains an amino acid activating agent (e.g., an alkaline liquid, a carbodiimide, and/or a uronium activating agent), capable of completing the activation of the amino acids. In certain embodiments, a reagent reservoir 27 contains a deprotection reagent, such as piperidine or trifluoroacetic acid. A reagent reservoir 28 may contain a solvent, such as dimethylformamide (DMF), that may be used, e.g., in a reagent removal step. While single reservoirs have been illustrated in FIG. 1 for simplicity, it should be understood that in FIG. 1, where single reservoirs are illustrated, multiple reservoirs (e.g., each containing different types of amino acids, different types of deprotection agents, etc.) could be used in place of the single reservoir.

In certain embodiments, peptides 20 comprise protection groups, for example, on the N-termini of the peptides. As used herein, the term "protection group" is given its ordinary meaning in the art. Protection groups include chemical moieties that are attached to or are configured to be attached to reactive groups (i.e., the protected groups) within a molecule (e.g., peptides) such that the protection groups prevent or otherwise inhibit the protected groups from reacting. Protection may occur by attaching the protection group to the molecule. Deprotection may occur when the protection group is removed from the molecule, for example, by a chemical transformation which removes the protection group.

In some embodiments, a plurality of peptides comprising protection groups may be bound to a solid support such that each peptide is immobilized on the solid support. For example, the peptides may be bound to the solid support via their C termini, thereby immobilizing the peptides.

In some embodiments, the process of adding amino acid residues to immobilized peptides comprises exposing a deprotection reagent to the immobilized peptides to remove at least a portion of the protection groups from at least a portion of the immobilized peptides. The deprotection reagent exposure step can be configured, in certain embodiments, such that side-chain protection groups are preserved, while N-termini protection groups are removed. For instance, in certain embodiments, the protection group used to protect the peptides comprises fluorenylmethyloxycarbonyl (Fmoc). In some such embodiments, a deprotection reagent comprising piperidine (e.g., a piperidine solution) may be exposed to the immobilized peptides such that the Fmoc protection groups are removed from at least a portion of the immobilized peptides. In some embodiments, the protection group used to protect the peptides comprises tert-butyloxycarbonyl (Boc). In some such embodiments, a deprotection reagent comprising trifluoroacetic acid may be exposed to the immobilized peptides such that the Boc protection groups are removed from at least a portion of the immobilized peptides. In some instances, the protection groups (e.g., tert-butoxycarbonyl, i.e., Boc) may be bound to the N-termini of the peptides.

In some embodiments, the process of adding amino acid residues to immobilized peptides comprises removing at least a portion of the deprotection reagent. In some embodiments, at least a portion of any reaction byproducts (e.g., protection groups) that may have formed during the deprotection step can be removed. In some instances, the deprotection reagent (and, in certain embodiments byproducts) may be removed by washing the peptides, solid support, and/or surrounding areas with a fluid (e.g., a liquid such as an aqueous or non-aqueous solvent, a supercritical fluid, and the like), for example stored in optional reservoir 28. In some instances, removing the deprotection reagent and reaction byproducts may improve the performance of subsequent steps (e.g., by preventing side reactions).

The process of adding amino acid residues to immobilized peptides comprises, in certain embodiments, exposing activated amino acids to the immobilized peptides such that at least a portion of the activated amino acids are bonded to the immobilized peptides to form newly-bonded amino acid residues. For example, the peptides may be exposed to activated amino acids that react with the deprotected N-termini of the peptides. In certain embodiments, amino acids can be activated for reaction with the deprotected peptides by mixing an amino acid-containing stream with an activation agent stream, as discussed in more detail below. In some instances, the amine group of the activated amino acid may be protected, such that addition of the amino acid results in an immobilized peptide with a protected N-terminus.

In some embodiments, the process of adding amino acid residues to immobilized peptides comprises removing at least a portion of the activated amino acids that do not bond to the immobilized peptides. In some embodiments, at least a portion of the reaction byproducts that may form during the activated amino acid exposure step may be removed. In some instances, the activated amino acids and byproducts may be removed by washing the peptides, solid support, and surrounding areas with a solvent.

It should be understood that the above-referenced steps are exemplary and an amino acid addition cycle need not necessarily comprise all of the above-referenced steps. Generally, an amino acid addition cycle includes any series of steps that results in the addition of an amino acid residue to a peptide.

In certain embodiments, during the amino acid addition steps, adding the amino acid can result in the peptide incorporating a single additional amino acid residue (i.e., a single amino acid residue can be added to the immobilized peptides such that a given peptide includes a single additional amino acid residue after the addition step). In some such embodiments, subsequent amino acid addition steps can be used to build peptides by adding amino acid residues individually until the desired peptide has been synthesized. In some embodiments, more than one amino acid residue (e.g., in the form of a peptide) may be added to a peptide immobilized on a solid support (i.e., a peptide comprising multiple amino acid residues can be added to a given immobilized peptide). Addition of peptides to immobilized peptides can be achieved through processes know to those of ordinary skill in the art (e.g., fragment condensation, chemical ligation). That is to say, during the amino acid addition step, adding an amino acid to an immobilized peptide can comprise adding a single amino acid residue to an immobilized peptide or adding a plurality of amino acid residues (e.g., as a peptide) to an immobilized peptide.

In some embodiments, amino acids can be added to peptides significantly faster than conventional methods. In certain embodiments, the total amount of time taken to perform the combination of steps may be influenced by the protection group. For instance, in certain embodiments in which the protection groups comprise fluorenylmethyloxycarbonyl (Fmoc), the total amount of time taken to perform the combination of all of the deprotection reagent exposing step, the deprotection reagent removal step, the activated amino acid exposing step, and the activated amino acid removal step is about 10 minutes or less, about 9 minutes or less, about 8 minutes or less, about 7 minutes or less, about 6 minutes or less, about 5 minutes or less, about 4 minutes or less, about 3 minutes or less, about 2 minutes or less, about 1 minute or less, from about 10 seconds to about 10 minutes, from about 10 seconds to about 9 minutes, from about 10 seconds to about 8 minutes, from about 10 seconds to about 7 minutes, from about 10 seconds to about 6 minutes, from about 10 seconds to about 5 minutes, from about 10 seconds to about 4 minutes, from about 10 seconds to about 3 minutes, from about 10 seconds to about 2 minutes, or from about 10 seconds to about 1 minute. In certain embodiments (including embodiments in which the protection groups comprise tert-butyloxycarbonyl (Boc), fluorenylmethyloxycarbonyl (Fmoc), and/or other types of protection groups), the total amount of time taken to perform the combination of all of the deprotection reagent exposing step, the deprotection reagent removal step, the activated amino acid exposing step, and the activated amino acid removal step is about 5 minutes or less, about 4 minutes or less, about 3 minutes or less, about 2 minutes or less, about 1 minute or less, from about 10 seconds to about 5 minutes, from about 10 seconds to about 4 minutes, from about 10 seconds to about 3 minutes, from about 10 seconds to about 2 minutes, or from about 10 seconds to about 1 minute.

In general, the total amount of time taken to perform the combination of all of the deprotection reagent exposing step, the deprotection reagent removal step, the activated amino acid exposing step, and the activated amino acid removal step is calculated by adding the amount of time it takes to perform the deprotection reagent exposing step to the amount of time it take to perform the deprotection reagent removal step and to the amount of time it take to perform the activated amino acid exposing step and to the amount of time it takes to perform the activated amino acid removal step.

In certain embodiments, the first amino acid addition step (and/or subsequent amino acid addition steps) may add amino acids at a relatively high yield. For example, certain embodiments include exposing amino acids to the immobilized peptides such that an amino acid residue is added to at least about 99%, at least about 99.9%, at least about 99.99%, or substantially 100% of the immobilized peptides. In certain embodiments, a second (and, in some embodiments, a third, a fourth, a fifth, and/or a subsequent) amino acid addition cycle can be performed which may include exposing amino acids to the immobilized peptides such that an amino acid residue is added to at least about 99%, at least about 99.9%, at least about 99.99%, or substantially 100% of the immobilized peptides. In certain embodiments, the use of processes and systems of the present invention may allow the addition of more than one amino acid to the immobilized peptides to occur relatively quickly (including within any of the time ranges disclosed above or elsewhere herein), while maintaining a high reaction yield.

In certain embodiments, one or more amino acid addition steps can be performed while little or no double incorporation (i.e., adding multiple copies of a desired amino acid (e.g., single amino acid residues or peptides) during a single addition step). For example, in certain embodiments, multiple copies of the desired amino acid are bonded to fewer than about 1% (or fewer than about 0.1%, fewer than about 0.01%, fewer than about 0.001%, fewer than about 0.0001%, fewer than about 0.00001%, or substantially none) of the immobilized peptides during a first (and/or second, third, fourth, fifth, and/or subsequent) amino acid addition step.

In some embodiments, multiple amino acid addition cycles can be performed. Performing multiple amino acid addition cycles can result in more than one single-amino-acid residue (or more than one peptide, and/or at least one single-amino-acid residue and at least one peptide) being added to a peptide. In certain embodiments a process for adding more than one amino acid to immobilized peptides may comprise performing a first amino acid addition cycle to add a first amino acid and performing a second amino acid addition cycle to add a second amino acid. In certain embodiments, third, fourth, fifth, and subsequent amino acid addition cycles may be performed to produce an immobilized peptide of any desired length. In some embodiments, at least about 10 amino acid addition cycles, at least about 50 amino acid addition cycles, or at least about 100 amino acid addition cycles are performed, resulting in the addition of at least about 10 amino acid residues, at least about 50 amino acid residues, or at least about 100 amino acid residues to the immobilized peptides. In certain such embodiments, a relatively high percentage of the amino acid addition cycles (e.g., at least about 50%, at least about 75%, at least about 90%, at least about 95%, or at least about 99% of such amino acid addition cycles) can be performed at high yield (e.g., at least about 99%, at least about 99.9%, at least about 99.99%, or substantially 100%). In some such embodiments, a relatively high percentage of the amino acid addition cycles (e.g., at least about 50%, at least about 75%, at least about 90%, at least about 95%, or at least about 99% of such amino acid addition cycles) can be performed quickly, for example, within any of the time ranges specified above or elsewhere herein. In some such embodiments, a relatively high percentage of the amino acid addition cycles (e.g., at least about 50%, at least about 75%, at least about 90%, at least about 95%, or at least about 99% of such amino acid addition cycles) can be performed with limited or no double incorporation, for example, within any of the double incorporation ranges specified above or elsewhere herein.

In embodiments in which there are more than one addition cycles, the total amount of time that passes between the end of an amino acid addition cycle and a subsequent amino acid addition cycle may be relatively short. For example, in certain embodiments in which fluorenylmethyloxycarbonyl protection groups are employed, the total amount of time between the ends of the first and second amino acid addition cycles is about 10 minutes or less, about 9 minutes or less, about 8 minutes or less, about 7 minutes or less, about 6 minutes or less, about 5 minutes or less, about 4 minutes or less, about 3 minutes or less, about 2 minutes or less, about 1 minute or less, from about 10 seconds to about 10 minutes, from about 10 seconds to about 9 minutes, from about 10 seconds to about 8 minutes, from about 10 seconds to about 7 minutes, from about 10 seconds to about 6 minutes, from about 10 seconds to about 5 minutes, from about 10 seconds to about 4 minutes, from about 10 seconds to about 3 minutes, from about 10 seconds to about 2 minutes, or from about 10 seconds to about 1 minute. In certain embodiments in which protection groups comprising, fluorenylmethyl-oxycarbonyl, tert-butyloxycarbonyl, or any other suitable protection group are employed, the total amount of time between the end of an amino acid addition cycle and a subsequent amino acid addition cycle may be about 5 minutes or less, about 4 minutes or less, about 3 minutes or less, about 2 minutes or less, about 1 minute or less, from about 10 seconds to about 5 minutes, from about 10 seconds to about 4 minutes, from about 10 seconds to about 3 minutes, from about 10 seconds to about 2 minutes, or from about 10 seconds to about 1 minute.

As mentioned above, certain aspects relate to processes and systems that allow the total time required for one or more addition cycles to be significantly reduced compared to previous solid phase peptide synthesis methods. Since the advent of continuous solid phase peptide synthesis over 30 years ago, continual efforts have focused on improving its utility and applicability. While these improvements have contributed to the commercial success of automated solid phase peptide synthesizers, reducing synthesis time still remains a significant barrier. Over 30 years of research and development in the field have been unable to produce fast synthesis techniques. Typical continuous solid phase peptide synthesis using Fmoc or Boc protection groups require 30 to 90 minutes to add a single amino acid. Certain processes and techniques have been discovered, with the context of the present invention, that address the long felt need to decrease synthesis time. For example, fast synthesis times may be achieved by employing specialized techniques for mixing, heating, and/or controlling pressure drop.

Certain steps in the amino acid addition cycle may require mixing of reagents. In some conventional systems, reagents are mixed a long time before exposure to the immobilized peptides, which may result in undesirable side reactions and/or reagent degradation prior to exposure to the immobilized peptides. In some instances, the side reactions and/or degradation adversely affects the yield and kinetics of step in the amino acid addition cycle (e.g., amino acid exposing step). In some conventional systems, reagents are mixed in the presence of the immobilized peptides, which may result, e.g., in slower reaction kinetics. One technique for achieving rapid peptide synthesis may involve merging reagent streams prior to, but within a short amount of time of, arrival at the immobilized peptides, as shown in FIG. 1.

In some embodiments, a process for adding amino acid residues to peptides comprises flowing a first stream comprising amino acids, flowing a second stream comprising an amino acid activating agent (e.g., an alkaline liquid, a carbodiimide, and/or a uronium activating agent). For example, referring back to FIG. 1, reagent reservoir 25 may comprise amino acids. Reagent reservoir 26 may comprise, in some such embodiments, an amino acid activating agent. The first and second streams may be merged to form a mixed fluid comprising activated amino acids. For example, referring to FIG. 1, amino acids from reservoir 25 can be flowed in first stream 30, and amino acid activating agent can be flowed in second stream 32. First stream 30 and second stream 32 can be mixed, for example, at point 34 of stream 40. The mixed fluid may comprise activated amino acids due to the activation of the amino acids by the amino acid activating agent.

In certain embodiments, after the amino acids have been activated, the immobilized peptides may be exposed to the mixed fluid within a relatively short period of time. For example, in certain embodiments, the plurality of peptides immobilized on the solid support may be exposed to the mixed fluid within about 30 seconds (or within about 15 seconds, within about 10 seconds, within about 5 seconds, within about 3 seconds, within about 2 seconds, within about 1 second, within about 0.1 seconds, or within about 0.01 seconds) after merging the first and second streams to form the mixed fluid.

In certain embodiments, merging reagent streams may be used in an amino acid addition cycle, as described herein. For example, a first fluid stream comprising amino acids and a second stream comprising an amino acid activating agent may be merged to form a mixed fluid comprising the activated amino acids within about 30 seconds prior to exposing the activated amino acids to peptides immobilized on a solid support. In some embodiments, in which more than one amino acid addition cycle is performed, one or more amino acid addition cycles (e.g., a first and a second amino acid addition cycle) may comprise merging a first fluid stream comprising amino acids and a second stream comprising an amino acid activating agent to form a mixed fluid comprising activated amino acids within about 30 seconds prior to exposing the amino acids to the solid support. It should be understood that merging reagent streams may be used in connection with any suitable step in the addition cycle and may be used in connection with one or more steps in an amino acid addition cycle.

In general, streams may be merged using any suitable technique known to those of skill in the art. In some embodiments, the streams may be merged by flowing the first stream and the second stream substantially simultaneously into a single stream (e.g., by merging channels through which the streams flow). Other merging methods may also be used.

Another technique for achieving fast synthesis times may involve heating a stream prior to, but within a short period of time of, arrival at the reactor. Supplying the reactor with a heated stream may alter the kinetics of a process occurring in the reactor. For example, exposing immobilized peptides, solid supports, or other synthesis components to a heated stream may alter the reaction kinetics and/or diffusion kinetics of the amino acid addition process. For example, exposing the peptides to a heated stream comprising activated amino acids may increase the rate at which amino acids are added to the peptides.

Thus, in some embodiments, a process for adding amino acid residues to peptides may comprise heating a stream comprising activated amino acids such that the temperature of the activated amino acids is increased by at least about 1° C. (or at least about 2° C., at least about 5° C., at least about 10° C., at least about 25° C., at least about 50° C., and/or less than or equal to about 100° C., and/or less than or equal to about 75° C.) prior to the heated amino acids being exposed to the immobilized peptides. In certain embodiments, a stream comprising any other component (e.g., a washing agent, a deprotection agent, or any other components) may be heated such that the temperature of the stream contents is increased by at least about 1° C. (or at least about 2° C., at least about 5° C., at least about 10° C., at least about 25° C., at least about 50° C., and/or less than or equal to about 100° C., and/or less than or equal to about 75° C.) prior to the stream contents being exposed to the immobilized peptides. In some instances, the heating step (e.g., the heating of the activated amino acids and/or the heating of any other component within a stream transported to the immobilized peptides) may be performed within about 30 seconds (or within about 15 seconds, within about 10 seconds, within about 5 seconds, within about 3 seconds, within about 2 seconds, within about 1 second, within about 0.1 seconds, or within about 0.01 seconds) of exposing the stream contents (e.g., the heated activated amino acids) to the immobilized peptides. In some such embodiments, and as illustrated in the exemplary embodiment of FIG. 1, such heating may be achieved by heating a location upstream of the immobilized peptides. In some such embodiments, the heating of the amino acids begins at least about 0.1 seconds, at least about 1 second, at least about 5 seconds, or at least about 10 seconds prior to exposure of the amino acids to the immobilized peptides. In certain embodiments, the amino acids are heated by at least about 1° C. (or at least about 2° C., at least about 5° C., at least about 10° C., at least about 25° C., at least about 50° C., and/or less than or equal to about 100° C., and/or less than or equal to about 75° C.) at least about 0.1 seconds, at least about 1 second, at least about 5 seconds, or at least about 10 seconds prior to the amino acids being exposed to the immobilized peptides.

Referring back to FIG. 1, for example, system 5 may comprise heating zone 42, within which the contents of stream 40 may be heated. Heating zone 42 may comprise a heater. In general, any suitable method of heating may be used to increase the temperature of a stream. For example, heating zone 42 may comprise a liquid bath (e.g., a water bath), a resistive heater, a gas convection-based heating element, or any other suitable heater. In some instances, the heating mechanism may be within a short distance of the immobilized peptides, for example, within about 5 meters, within about 1 meter, within about 50 cm, or within about 10 cm.

In some embodiments, including those illustrated in FIG. 1, both the heating of the amino acids and the merging of the amino acids with the amino acid activating agent (e.g., an alkaline liquid, a carbodiimide, and/or a uronium activating agent) can be performed before and within a relatively short time of the amino acids contacting the immobilized peptides. Heating the amino acids may be performed before, during, and/or after merging the stream comprising the amino acids with the stream comprising the amino acid activating agent.

In certain embodiments, heating a stream just prior to being exposed to the immobilized peptides (as opposed to heating the stream long before transport of the stream contents to the immobilized peptides) may minimize the thermal degradation of one or more reagents (such as, for example, the amino acids that are to be added to the peptides and/or the deprotection reagent) in the stream. Of course, as discussed above, heating a stream prior to arrival of the stream components can enhance the speed with which a reaction or washing step may be performed.

In some embodiments, a heating step may be used in an amino acid addition cycle, as described herein. For example, heating the activated amino acids, such that the temperature of the activated amino acids is increased by at least about 1° C., may be performed prior to and within about 30 seconds (or within any of the other time ranges mentioned elsewhere) of exposing the activated amino acids to the immobilized peptides. In certain embodiments, in which more than one amino acid addition cycle is performed, one or more amino acid addition cycles (e.g., a first and a second amino acid addition cycle) may comprise heating the activated amino acids prior to and within about 30 seconds (or within any of the other time ranges mentioned elsewhere) of exposing the activated amino acids to the immobilized peptides. It should be understood that a heating step may be used in connection with any suitable step in the addition cycle and may be used in connection with one or more steps of any individual addition cycle or with all steps of a series of addition cycles.

As noted above, in some embodiments, heating a stream may increase the temperature of the stream contents (e.g., may increase the temperature of amino acids within the stream) by at least about 1° C., at least about 2° C., at least about 5° C., at least about 10° C., at least about 25° C., or at least about 50° C. In some instances, heating a stream may increase the temperature of the stream contents (e.g., may increase the temperature of amino acids within the stream) by less than or equal to about 100° C. or less than or equal to about 75° C. Combinations of the above-referenced ranges are also possible (e.g., at least about 1° C. and less than or equal to about 100° C., etc.).

Systems and methods for reducing pressure drop across the immobilized peptides may be used, according to certain embodiments, to improve the speed of peptide synthesis. In some embodiments, the flow rate of reagents across the immobilized peptides may influence the speed of peptide synthesis. For example, the time required for one or more steps in an amino acid addition cycle (e.g., deprotection reagent exposing step, deprotection reagent removal step, activated amino acid exposing step, activated amino acid removal step) may decrease with increasing flow rate. In general, the use of high flow rates ensures that the concentration of reagent near the immobilized peptides is not depleted as severely as might be observed when low flow rates are employed. In many traditional continuous solid phase peptide synthesis systems, the flow rate is limited by the pressure drop across the reactor. Pressure drop may occur due to expansion of the solid support during synthesis and/or due to improper sizing of process equipment. In certain embodiments, the pressure drop across the solid support during an amino acid addition cycle may not exceed about 700 psi for more than about 5% (or for more than about 1%) of the time period during which the cycle is performed. For example, in certain embodiments, during each step of an amino acid addition cycle (e.g. the deprotection reagent exposing step, the deprotection reagent removal step, the activated amino acid exposing step, and the activated amino acid removal step) the pressure drop across the solid support may not exceed about 700 psi for more than about 5% (or for more than about 1%) of the time period during which the step is performed. In embodiments in which more than one addition cycle is performed, the pressure drop during one or more addition cycles (e.g., the first and second amino acid addition cycle) may not exceed about 700 psi for more than about 5% (or for more than about 1%) of the time period during which the cycle is performed.

In some embodiments, the pressure drop across reactor during each step of an amino acid addition cycle and/or during one or more addition cycles may not exceed about 700 psi, about 600 psi, about 500 psi, about 400 psi, about 250 psi, about 100 psi, or about 50 psi for more than about 5% (or for more than about 1%) of the time period during which the step is performed.

In certain embodiments, the pressure drop across reactor may be reduced by using a process vessel (e.g., the column of a packed column) with a desirable aspect ratio. Generally, the aspect ratio of a process vessel is the ratio of the length of the vessel (substantially parallel to the direction of flow through the vessel) to the shortest width of the vessel (measured perpendicular to the length of the vessel). As an example, in the case of a cylindrical vessel, the aspect ratio would be the ratio of the height of the cylinder to the cross-sectional diameter of the cylinder. Referring back to FIG. 1, for example, the aspect ratio of reactor 10 would be the ratio of the length of dimension A to the length of dimension B (i.e., A:B). In some embodiments, the aspect ratio of the reactor may be less than or equal to about 20:1, less than or equal to about 10:1, less than or equal to about 5:1, less than or equal to about 3:1, less than or equal to about 2:1, less than or equal to about 1:1, less than or equal to about 0.5:1, less than or equal to about 0.2:1, or less than or equal to about 0.1:1 (and/or, in certain embodiments, as low as 0.01:1, or lower).

In some embodiments, relatively short addition cycles with high yields and/or limited and/or no double incorporation may be achieved by employing one or more of the techniques described herein. For example, certain of the systems and methods described herein may allow the amino acid exposing step (i.e., the step of exposing the activated amino acids to the immobilized peptides) to be performed (e.g., while achieving the high yields and/or avoiding double incorporation to any of the degrees described herein) in about 1 minute or less (e.g., about 30 seconds or less, about 15 seconds or less, about 10 seconds or less, about 7 seconds or less, or about 5 seconds or less, and/or, in certain embodiments, in as little as 1 second, or less). In some instances, certain of the systems and methods described herein may allow the deprotection reagent removal step and/or the activated amino acid removal step to be performed in about 2 minutes or less (e.g., about 1.5 minutes or less, about 1 minute or less, about 45 seconds or less, about 30 seconds or less, about 15 seconds or less, about 10 seconds or less, about 5 seconds or less, and/or, in certain embodiments, in as little as 1 second, or less). In certain embodiments, certain of the systems and methods described herein may allow the deprotection reagent exposing step (i.e., the step of exposing the immobilized peptides to the deprotection reagent) to be performed in about 20 seconds or less (e.g., about 15 seconds or less, about 10 seconds or less, about 8 seconds or less, about 5 seconds or less, about 1 second or less, and/or, in certain embodiments, in as little as 0.5 seconds, or less).

In certain cases, the time required for peptide synthesis may be influenced by the choice of protection group. For example, the use of Fmoc protection groups is generally understood to require longer synthesis cycle times. However, the systems and methods described herein can be used to perform fast amino acid addition, even when Fmoc protection group chemistries are employed. In some embodiments, the total time for an amino acid addition cycle may be low, regardless of the type of protection group that is being used.

In general, any protection group known to those of ordinary skill in the art can be used. Non-limiting examples of protection groups (e.g., n-terminal protection groups) include fluorenylmethyloxycarbonyl, tert-butyloxycarbonyl, allyloxycarbonyl (alloc), carboxybenzyl, and photolabile protection groups. In certain embodiments, immobilized peptides comprise fluorenylmethyloxycarbonyl protection groups. In some embodiments, immobilized peptides comprise tert-butyloxycarbonyl protection groups.

As described elsewhere, an amino acid activating agent may be used to activate or complete the activation of amino acids prior to exposing the amino acids to immobilized peptides. Any suitable amino acid activating agent may be used. In certain embodiments, the amino acid activating agent comprises an alkaline liquid. The amino acid activating agent comprises, in some embodiments, a carbodiimide, such as N,N'-dicyclohexylcarbodiimide (DCC), 1-ethyl-3-(3-dimethylaminopropyl)carbodiimide (EDC), and the like. In certain embodiments, the amino acid activating agent comprises a uronium activating agent, such as O-(Benzotriazol-1-yl)-N,N,N',N'-tetramethyluronium hexafluorophosphate (HBTU); 2-(7-Aza-1H-benzotriazole-1-yl)-1,1,3,3-tetramethyluronium hexafluorophosphate (HATU); 1-[(1-(Cyano-2-ethoxy-2-oxoethylideneaminooxy) dimethylaminomorpholino)] uronium hexafluorophosphate (COMU); and the like.

As described elsewhere, peptides may be immobilized on a solid support. In general, any solid support may be used with any of the addition cycles described herein. Non-limiting examples of solid support materials include polystyrene (e.g., in resin form such as microporous polystyrene resin, mesoporous polystyrene resin, macroporous polystyrene resin), glass, polysaccharides (e.g., cellulose, agarose), polyacrylamide resins, polyethylene glycol, or copolymer resins (e.g., comprising polyethylene glycol, polystyrene, etc.).

The solid support may have any suitable form factor. For example, the solid support can be in the form of beads, particles, fibers, or in any other suitable form factor.

In some embodiments, the solid support may be porous. For example, in some embodiments macroporous materials (e.g., macroporous polystyrene resins), mesoporous materials, and/or microporous materials (e.g., microporous polystyrene resin) may be employed as a solid support. The terms "macroporous," "mesoporous," and "microporous," when used in relation to solid supports for peptide synthesis, are known to those of ordinary skill in the art and are used herein in consistent fashion with their description in the International Union of Pure and Applied Chemistry (IUPAC) Compendium of Chemical Terminology, Version 2.3.2, Aug. 19, 2012 (informally known as the "Gold Book"). Generally, microporous materials include those having pores with cross-sectional diameters of less than about 2 nanometers. Mesoporous materials include those having pores with cross-sectional diameters of from about 2 nanometers to about 50 nanometers. Macroporous materials include those having pores with cross-sectional diameters of greater than about 50 nanometers and as large as 1 micrometer.

One advantage of the inventive systems and methods described herein is that they can be used with standard solid support materials without degradation in performance. For example, in certain embodiments, a standard commercial polystyrene resin support can be used. In many previous systems, such supports collapsed when used in flow-based solid phase peptide synthesis systems, causing an increase in pressure drop. As the resin swells during synthesis, it becomes increasingly likely to collapse, which causes an increase in the pressure drop across the resin, requiring an increase in applied pressure to maintain a constant flow rate. The increase in applied pressure can lead to more severe collapse of the resin, leading to a positive feedback effect in which the pressure applied to the fluid must be repeatedly increased. At sufficiently high pressures, the resin may extrude through any frit or other system used to confine it. The systems and methods described herein can be used to manage pressure drop such that the resin (including standard polystyrene resins and other standard resins) do not collapse during synthesis or collapse only to a degree that does not result in the positive feedback effect described above, leading to a more stable and controllable system. In certain embodiments, the solid support is contained within a packed column.

As used herein, the term "peptide" has its ordinary meaning in the art and may refer to amides derived from two or more amino carboxylic acid molecules (the same or different) by formation of a covalent bond from the carbonyl carbon of one to the nitrogen atom of another with formal loss of water. An "amino acid residue" also has its ordinary meaning in the art and refers to the composition of an amino acid (either as a single amino acid or as part of a peptide) after it has combined with a peptide, another amino acid, or an amino acid residue. Generally, when an amino acid combines with another amino acid or amino acid residue, water is removed, and what remains of the amino acid is called an amino acid residue. The term "amino acid" also has its ordinary meaning in the art and may include proteogenic and non-proteogenic amino acids.

The following examples are intended to illustrate certain embodiments of the present invention, but do not exemplify the full scope of the invention.

Example 1

This example describes a flow based platform for rapid Fmoc solid phase peptide synthesis, in which an amino acid was incorporated in steps of under five minutes. In this example, each step for amino acid addition (e.g., amide bond formation, wash, and N-termini deprotection) was carried out under a constant stream of fluid passed over a resin confined in a small, fritted plastic tube. Flow methods, as opposed to commonly used batch methods, allowed for the consistent rapid preheating, addition, and removal of solvents and reagents. The consistent rapid preheating, addition, and removal of solvents and reagents allowed a 5 minute cycle time, which included a 30 second amide-bond formation step. A number of model peptides were prepared, without double coupling or double deprotection. In addition, good yields and high purity, as shown by liquid chromatography-mass spectrometry (LC-MS), were achieved. This approach was also applied to the synthesis of a 58-residue protein from three polypeptide segments. The longest fragment, a 27 residue peptide, was prepared in 2.3 hours, which was 10 fold faster than conventional Fmoc methods. It is believed that automating various processing steps, increasing flow rate, reducing unnecessarily long wash times, and using a smaller aspect ratio reactor would substantially reduce the synthesis times reported here.

Figure 2A:
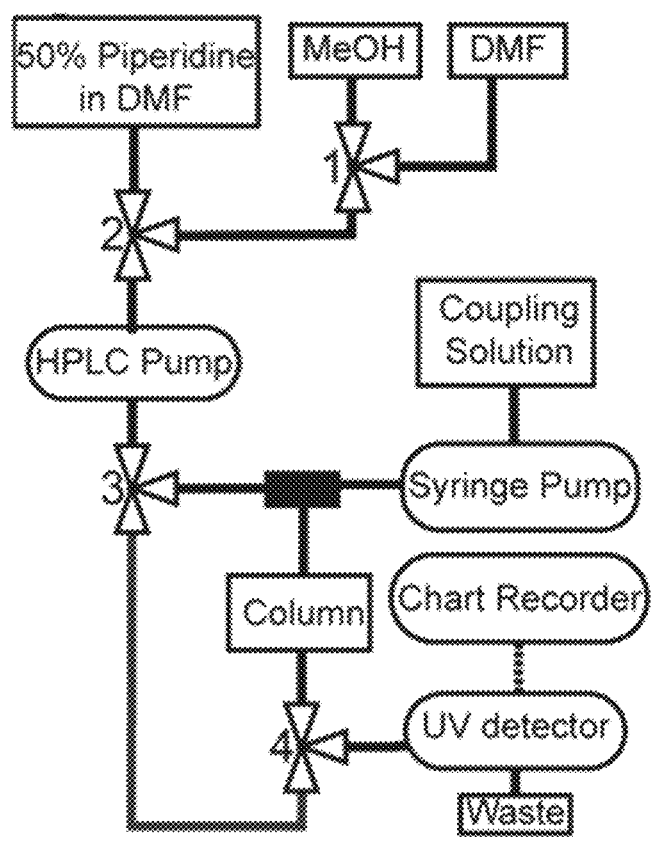
FIG. 2A is, according to certain embodiments, an exemplary schematic diagram of a peptide synthesis system.
Figure 2B:
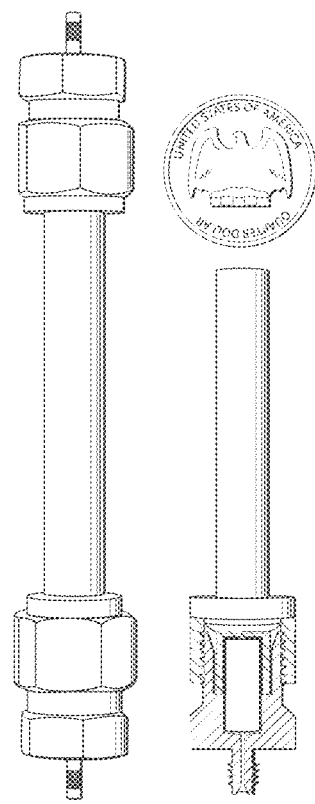
FIG. 2B is, according to certain embodiments, a photograph of an exemplary peptide synthesis system.

As shown in FIG. 2A, a high pressure liquid chromatography (HPLC) pump was used to deliver either a piperidine deprotection solution or a dimethylformamide (DMF) wash solvent to the reaction vessel. A manually actuated 3-way valve was used to select which reagent was delivered to the reaction vessel. The HPLC pump outlet was attached to the reaction vessel via a luerlock quick connect. For the coupling step, the quick connect was manually moved to a syringe pump, which delivered a solution of activated amino acid. It is believed that even faster performance than that reported here could be achieved by automating this step. The reactor effluent was passed through a UV detector to continuously monitor the absorbance at 304 nm, a region where Fmoc amino acids absorb strongly. The reactor was designed to be simple and easy to construct. A ¼" inner diameter by 3.5" long perfluoroalkoxy tube with Swagelok reducing unions as the inlet and outlet was used. A frit was positioned in the outlet using a short piece of tubing with a ¼ in. outer diameter. Installation of the outlet fitting and concurrent compression of the ferrule and tube sealed the frit in place as seen in FIG. 2B. The total volume of the reactor was about 2.5 mL. This design held up to 100 mg of resin and was used to prepare peptides up to 27 residues in length.

Figure 2C:
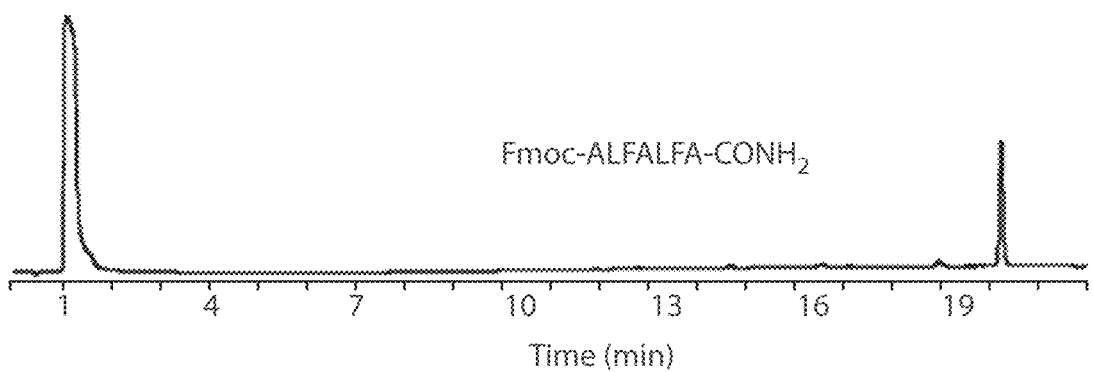
FIG. 2C is, according to certain embodiments, a chromatogram for a synthesized peptide Fmoc-ALFALFA-CONH$_2$ (SEQ ID NO: 1)
Figure 2D:
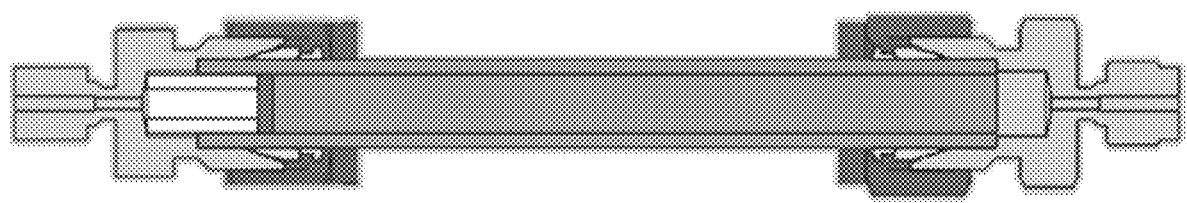
FIG. 2D is, according to certain embodiments, an exemplary schematic diagram of a reactor.

To verify the feasibility of Fmoc SPPS with the flow based SPPS system, the model peptide Fmoc-ALFALFA-CONH2 (SEQ ID NO: 1) was synthesized on a 0.1 mmol scale using 100 mg of resin. Based on an initial estimate, a 2 minute DMF wash at 10 mL/min, a 2 minute Fmoc deprotection step at 6 mL/min, and another DMF wash, and a 6 minute room temperature coupling with activated amino acid delivered at 1 mL/min were chosen as the starting point for an amino acid addition cycle. This sequence allowed efficient peptide synthesis in 12 minutes per residue. The reverse phase (RP)-HPLC trace for the crude peptide is shown in FIG. 2C.

Figure 3A:
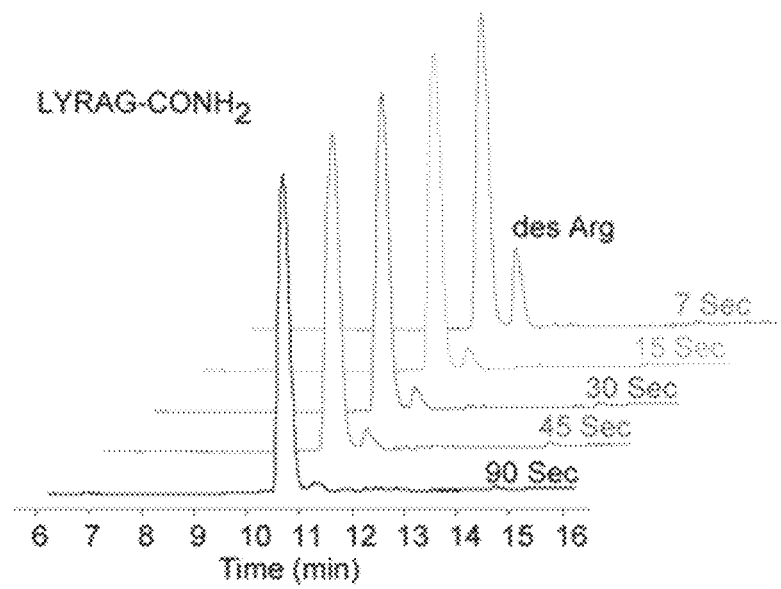
FIG. 3A is, according to one set of embodiments, chromatograms of LYRAG-CONH$_2$ (SEQ ID NO: 2) peptides synthesized with different activated amino acid exposing times.
Figure 3B:
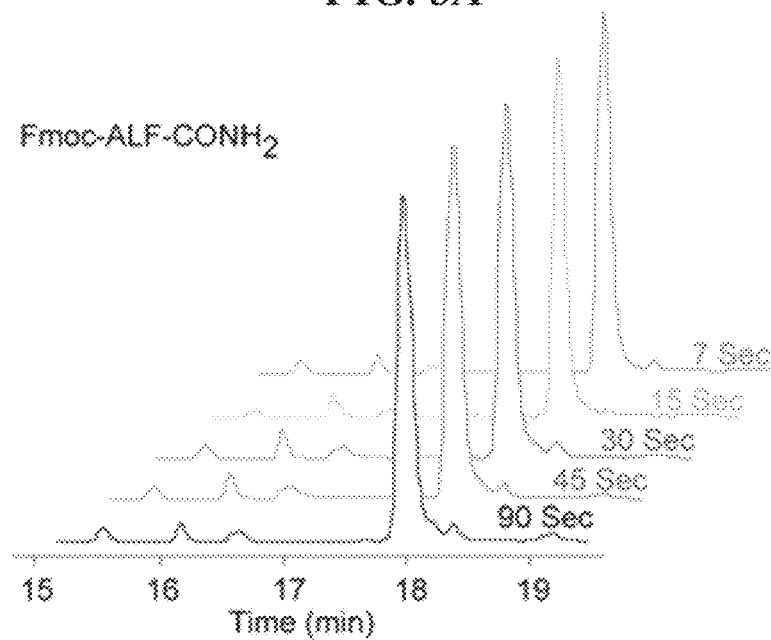
FIG. 3B is, according to one set of embodiments, chromatograms of Fmoc-ALF-CONH$_2$ peptides synthesized with different activated amino acid exposing times.
Figure 3C:
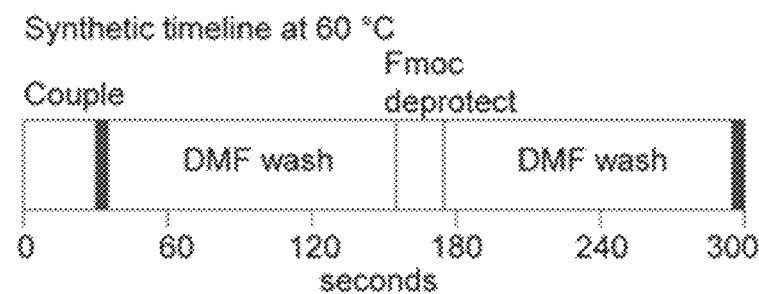
FIG. 3C is, according to one set of embodiments, an exemplary synthetic timeline.

After validating this approach, improved wash step, Fmoc removal, and coupling times were determined. All subsequent studies were carried out at 60° C. to reduce the cycle time without significantly increasing formation of side products. The final synthetic timeline, which was used in all subsequent experiments, is shown in FIG. 3C. The final synthetic timeline has a 2 minute DMF wash at 10 mL/min, a 20 second Fmoc deprotection step at 10 mL/min, another 2 minute DMF wash, and a 30 second coupling step with activated amino acid delivered at 12 mL/min. This approach was studied by synthesizing the peptide ACP(65-74). This peptide served as a model to validate the flow based SPPS platform, because ACP(65-74) was considered difficult to prepare. It is believed that substantial reductions in synthesis times could be achieved when synthesizing peptides that are easier to prepare.

In conventional systems, the main synthetic impurity in the synthesis of ACP(65-74) is a chromatographically resolved Val deletion. The LCMS data for the synthesis of ACP(65-74) with the flow based SPPS platform methodology, as well as two controls, is shown in FIGS. 4A-4D. Using the adjusted protocol and the HATU coupling agent, a minor Val deletion product was observed. When using HBTU, more Val deletion was observed, which is consistent with prior reports. ACP(65-74) synthesized with the flow based SPPS platform, but at room temperature, showed large Val and Gln deletions, confirming that temperature is important. No major differences between the product composition from the room temperature synthesis and an analogous batch synthesis were observed. Two additional "difficult" peptides, a conotoxin variant and a fragment of the HIV-1 protease, were also synthesized. The LCMS data is shown in FIGS. 5A-5B. Both of these peptides contained cysteine residues that were observed to racemize during activation. Therefore, model studies using the peptide GCF were carried out. Using the model study, several conditions that produced less than 1% diastereomer, as shown in FIGS. 6A-6E, were found. This level of racemization is consistent with literature for Fmoc protocols.

Figure 7A:
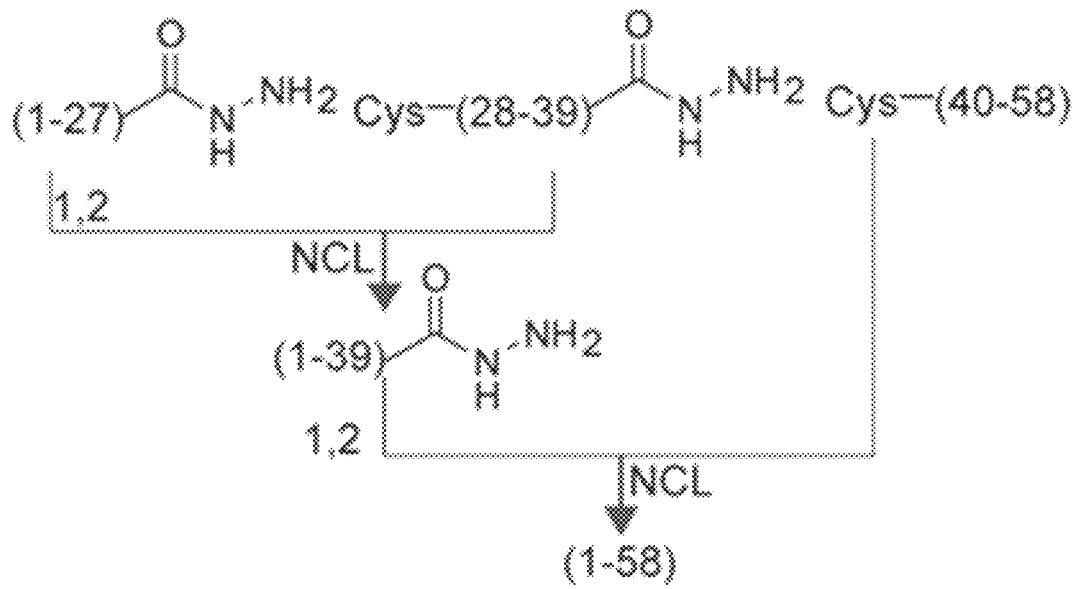
FIG. 7A is, according to certain embodiments, an exemplary scheme for the chemical ligation of an affibody protein from three peptide fragments.
Figure 7B:
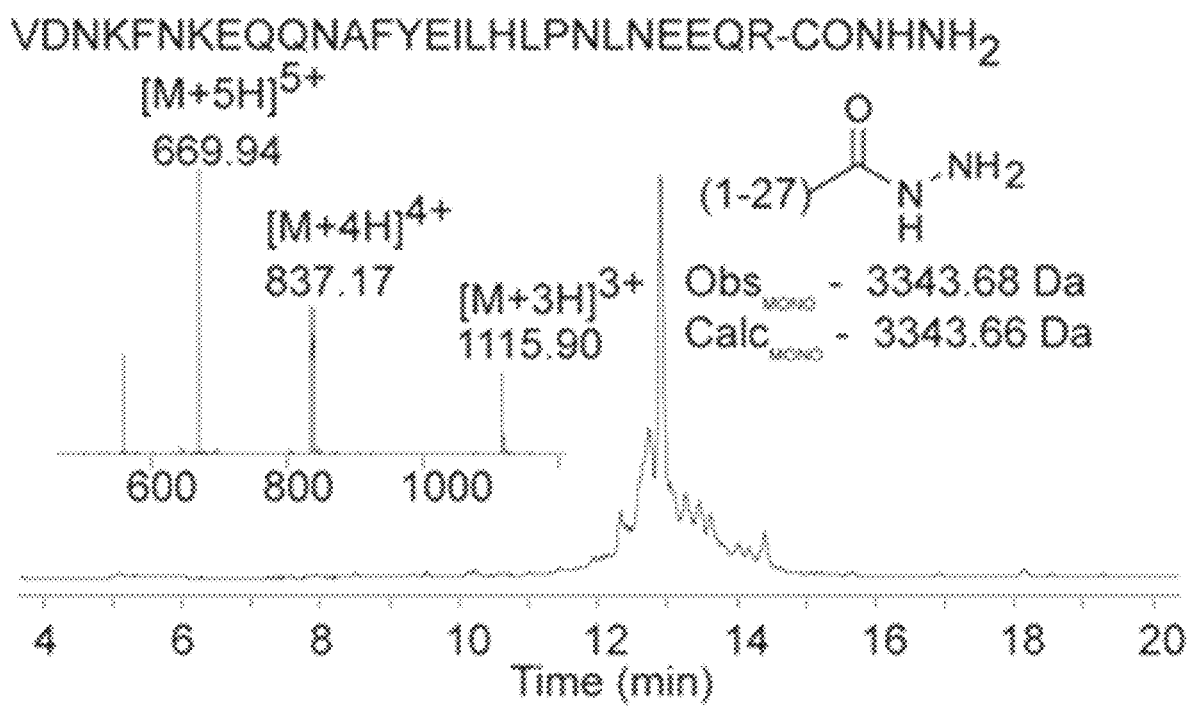
FIG. 7B is, according to certain embodiments, a chromatogram and mass spectrum for a first affibody fragment (SEQ ID NO: 6)
Figure 7C:
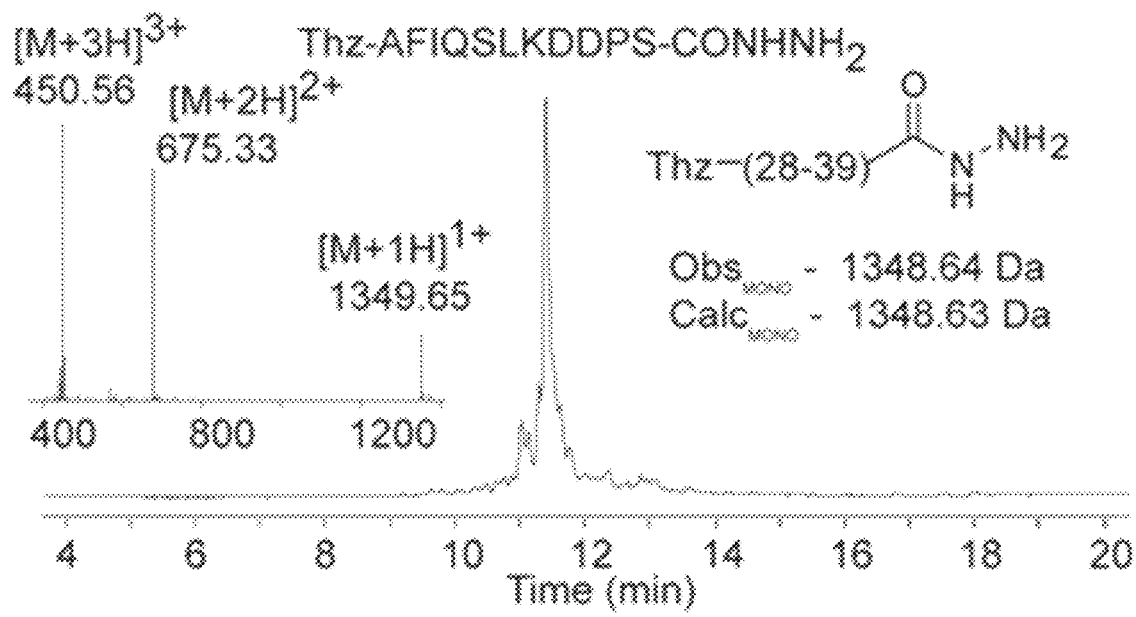
FIG. 7C is, according to certain embodiments, a chromatogram and mass spectrum for a second affibody fragment (SEQ ID NO: 7)
Figure 7D:
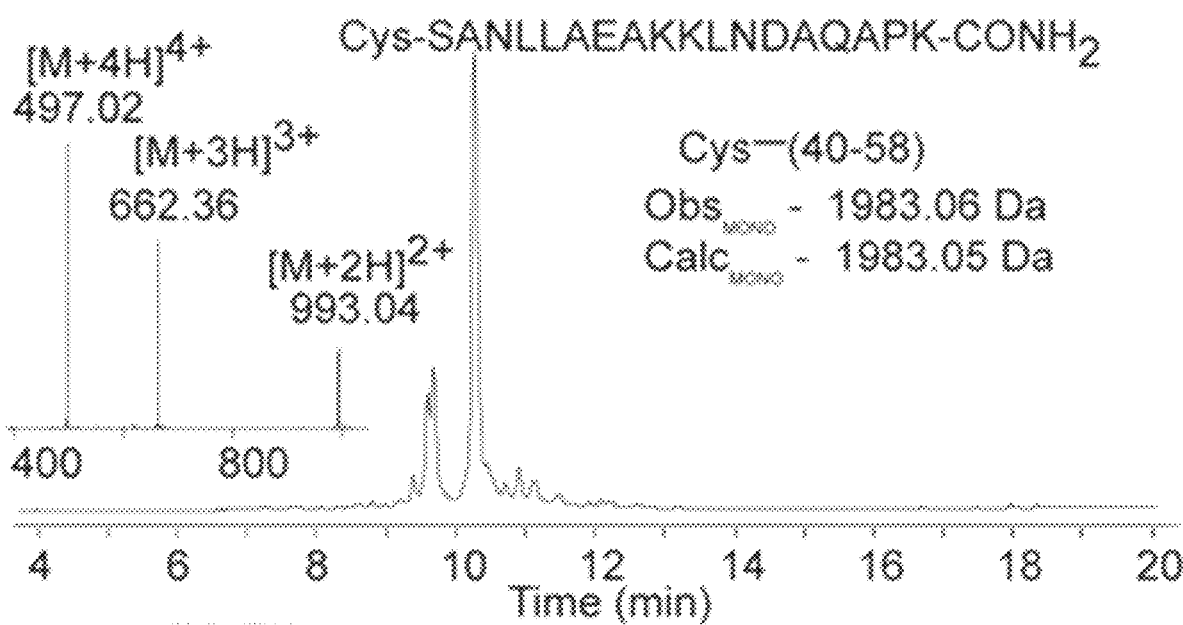
FIG. 7D is, according to certain embodiments, a chromatogram and mass spectrum for a third affibody peptide fragment (SEQ ID NO: 8)
Figure 7E:
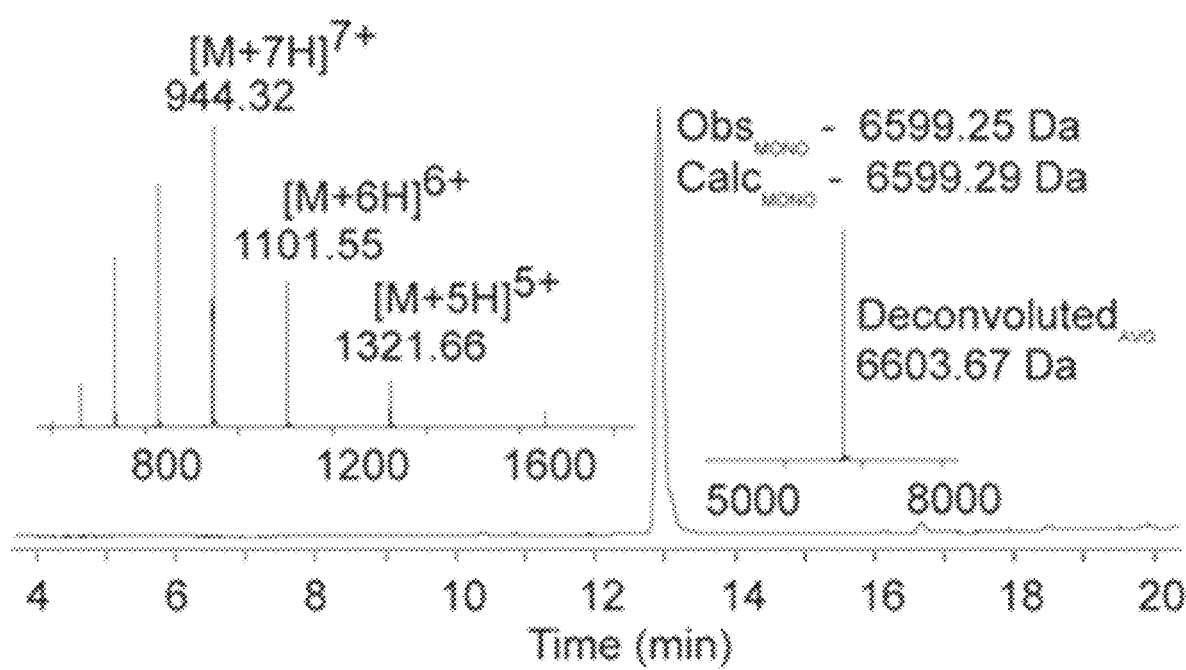
FIG. 7E is, according to certain embodiments, a chromatogram and mass spectrum for the purified affibody.
Figure 8A:
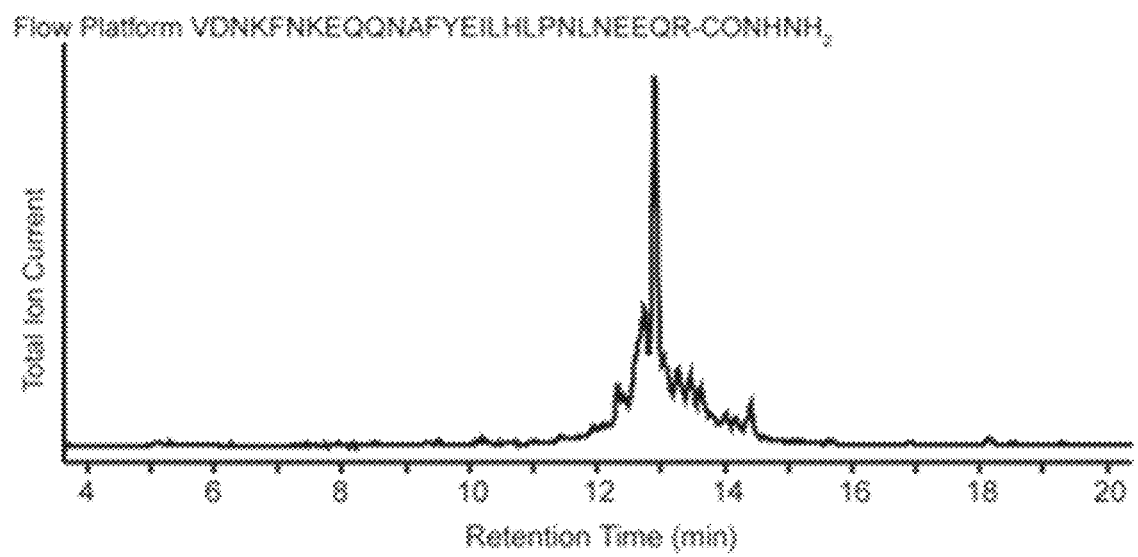
FIG. 8A is, according to certain embodiments, a total ion chromatogram for the N-terminal affibody fragment for a flow arrangement using Boc N-terminal protecting groups (SEQ ID NO: 9)
Figure 8B:
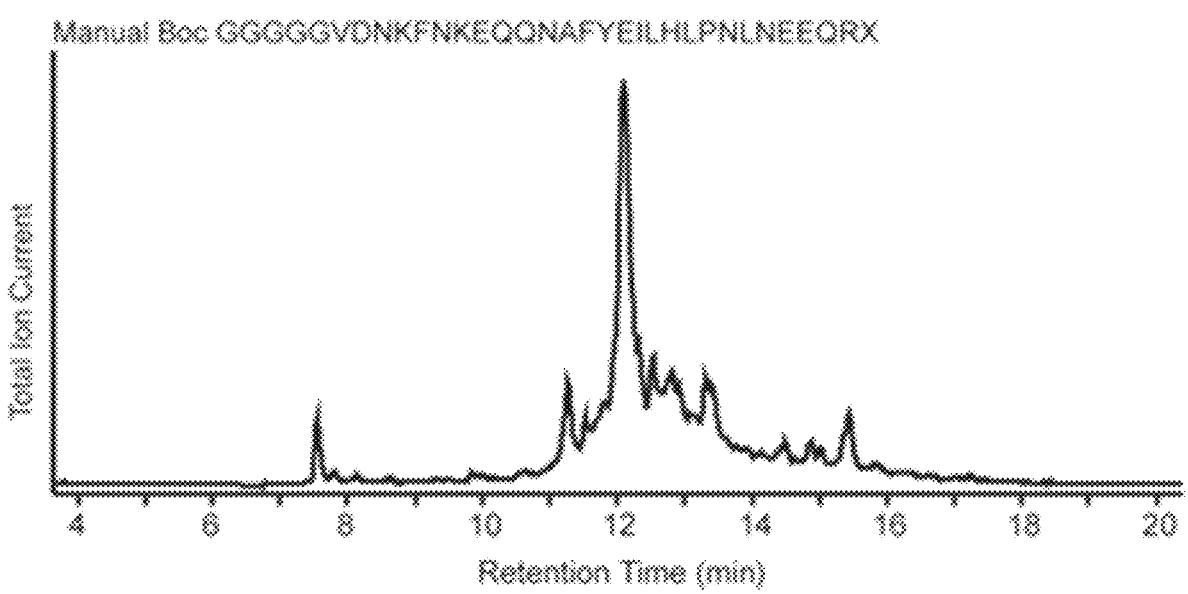
FIG. 8B is, according to certain embodiments, a total ion chromatogram for the N-terminal affibody fragment for a manual arrangement using Boc N-terminal protecting groups (SEQ ID NO: 10)
Figure 8C:
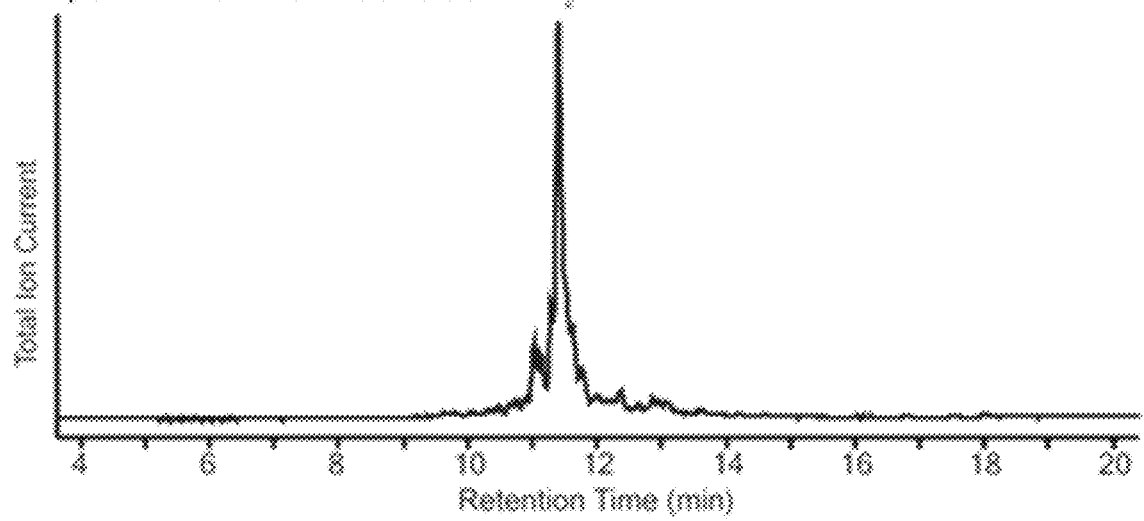
FIG. 8C is, according to certain embodiments, a total ion chromatogram for the middle affibody fragment for a flow arrangement (SEQ ID NO: 11)
Figure 8D:
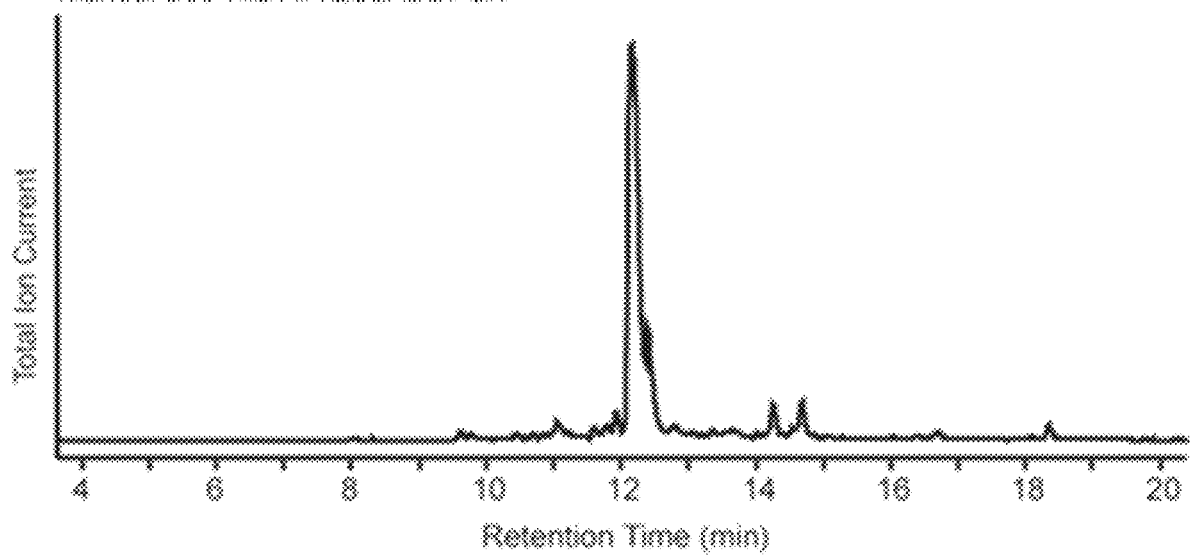
FIG. 8D is, according to certain embodiments, a total ion chromatogram for the middle affibody fragment for a manual arrangement (SEQ ID NO: 12)
Figure 8E:
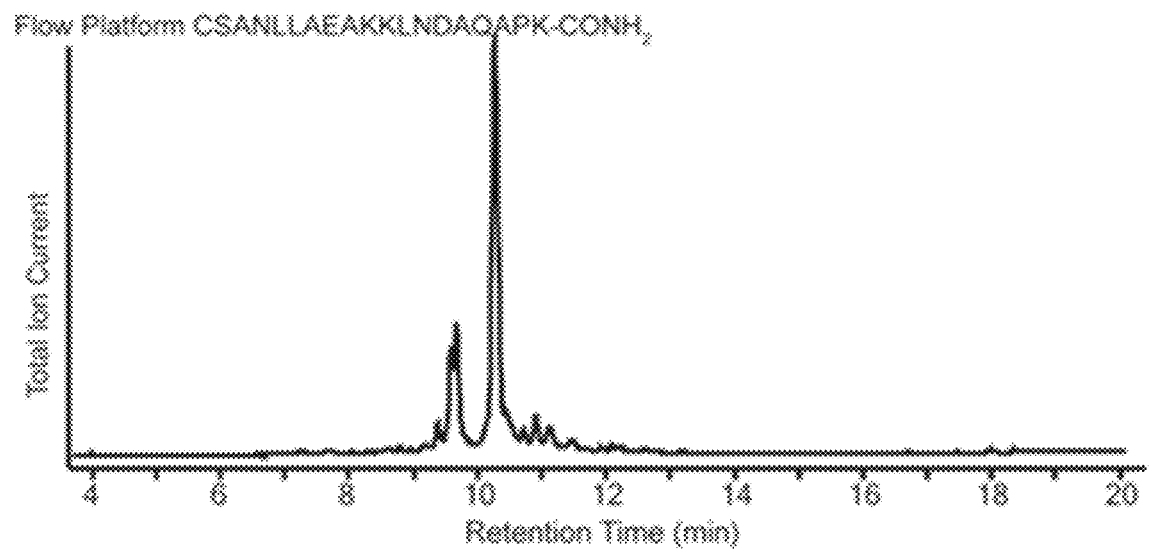
FIG. 8E is, according to certain embodiments, a total ion chromatogram for the C-terminal affibody fragment for affibody peptides for a flow arrangement (SEQ ID NO: 13)
Figure 8F:
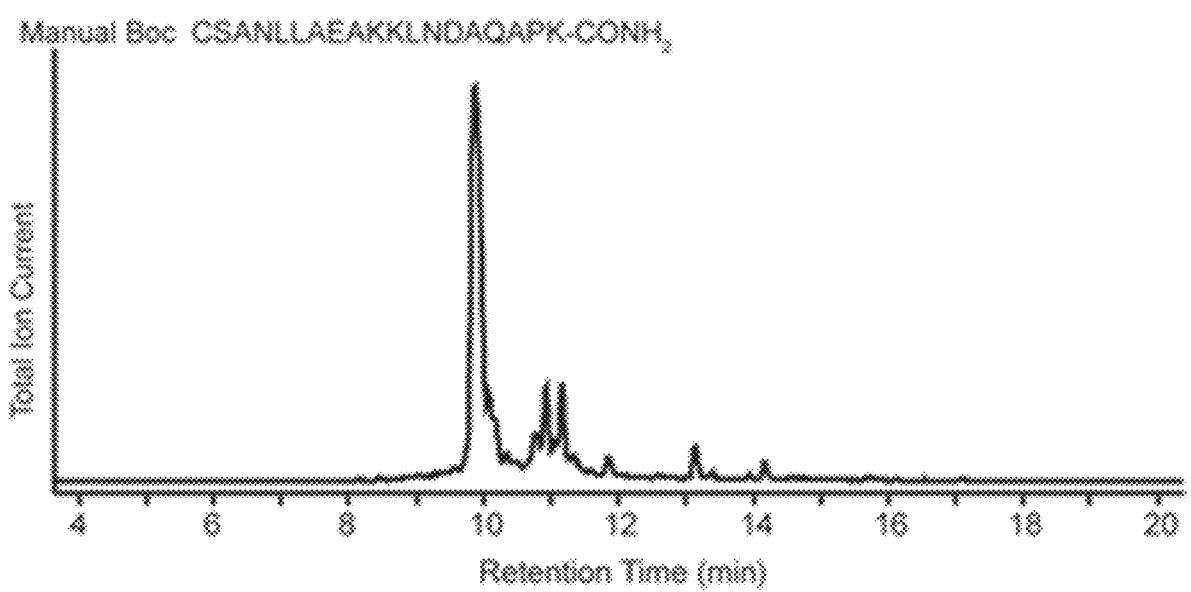
FIG. 8F is, according to certain embodiments, a total ion chromatogram for the C-terminal affibody fragment for affibody peptides for a manual arrangement (SEQ ID NO: 14)
Figure 9A:
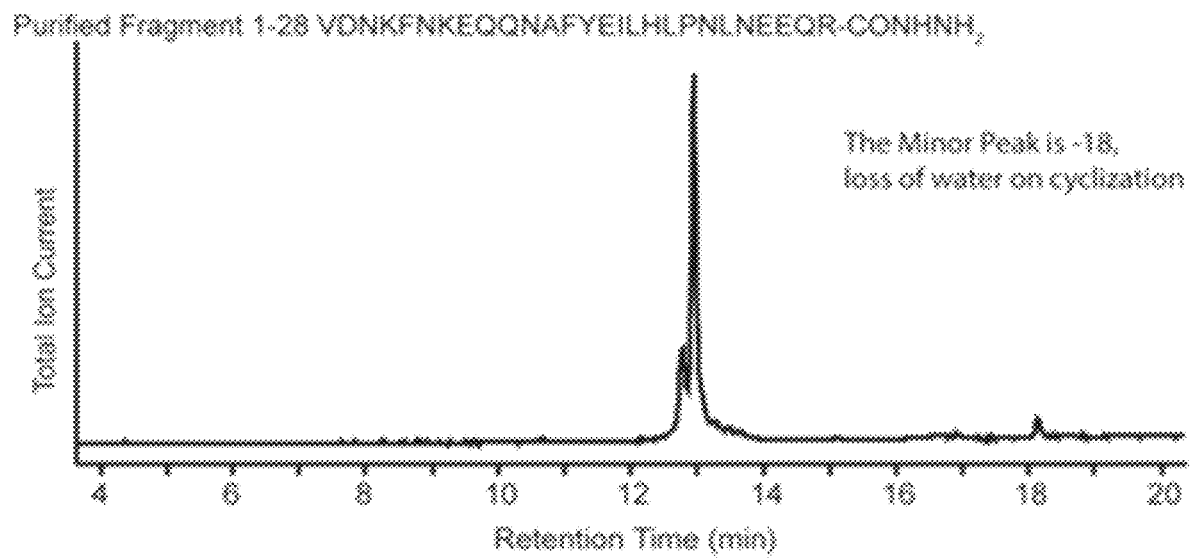
FIG. 9A is, according to certain embodiments, a total ion chromatogram for a purified first affibody fragment (SEQ ID NO: 6)
Figure 9B:
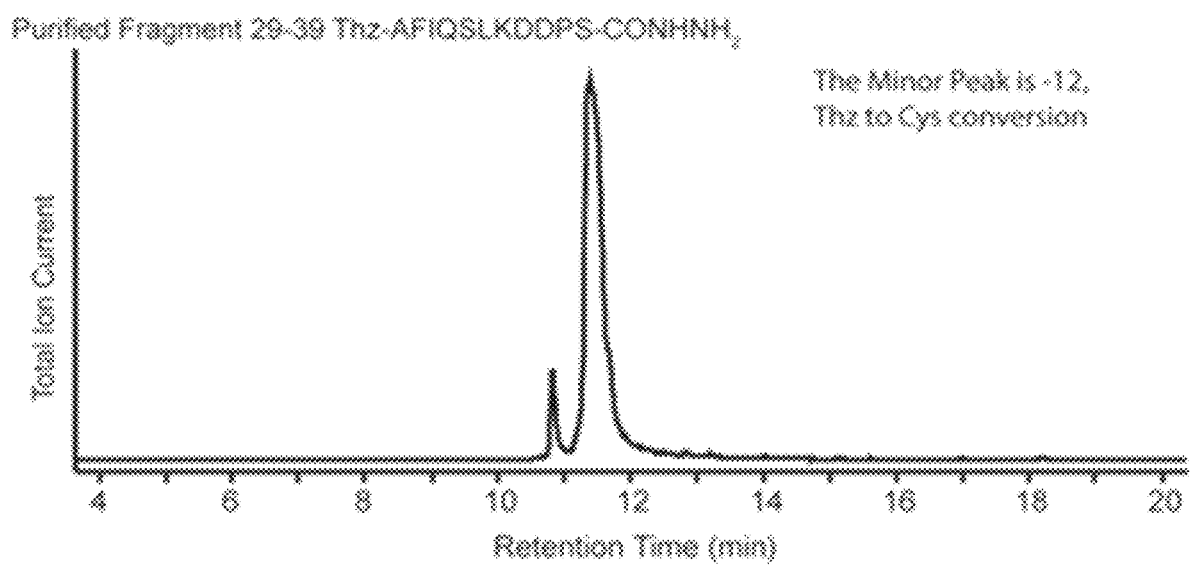
FIG. 9B is, according to certain embodiments, a total ion chromatogram for a purified second affibody fragment (SEQ ID NO: 7)
Figure 9C:
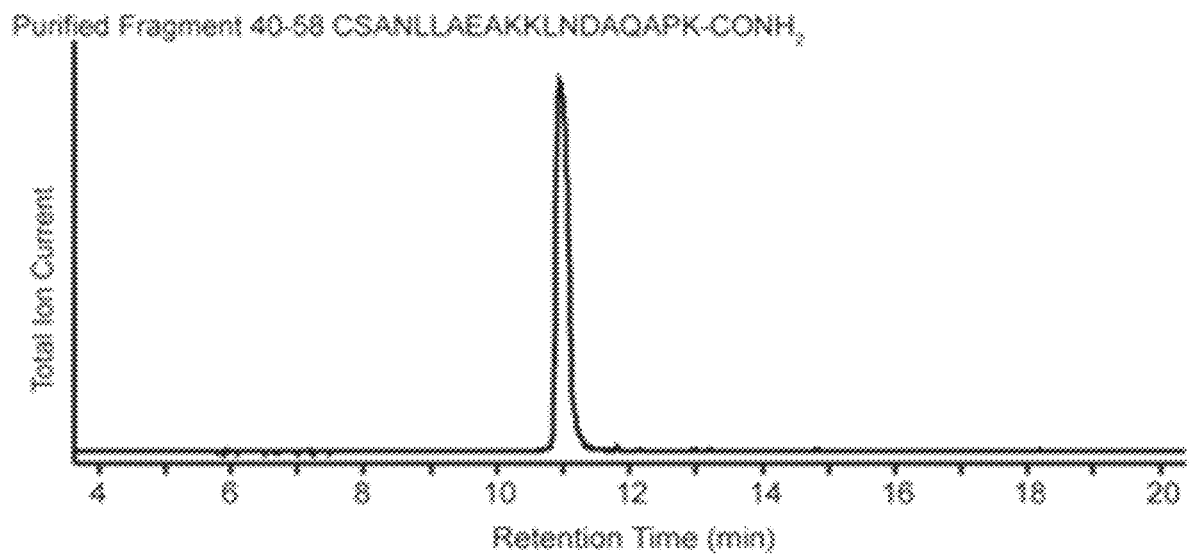
FIG. 9C is, according to certain embodiments, a total ion chromatogram for a purified third affibody fragment (SEQ ID NO: 8)
Figure 9D:
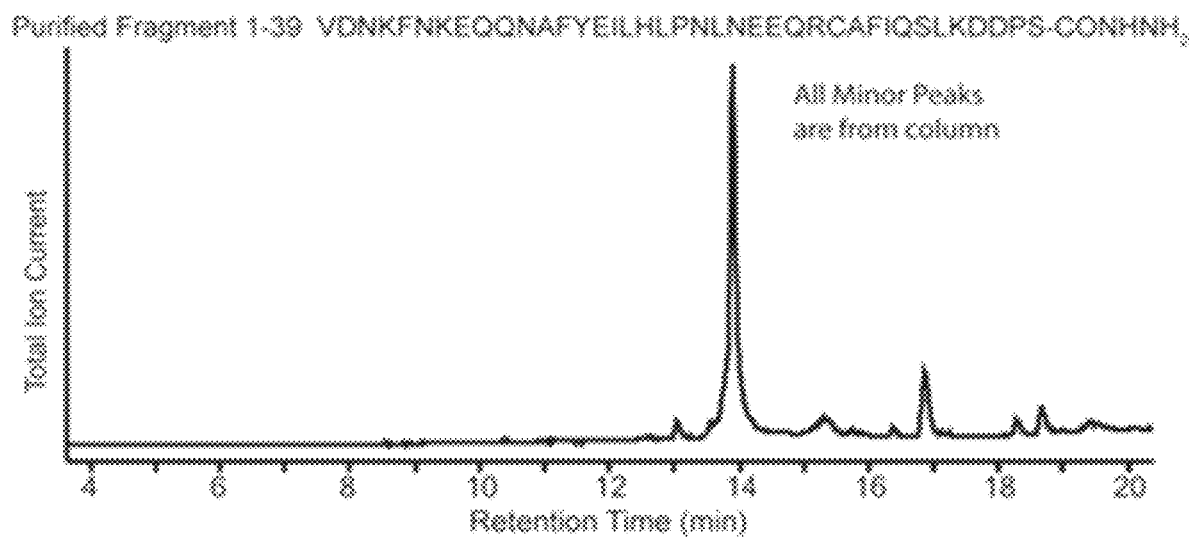
FIG. 9D is, according to certain embodiments, a total ion chromatogram for the purified affibody fragment from the ligation of the first and second fragment (SEQ ID NO: 15)
Figure 9E:
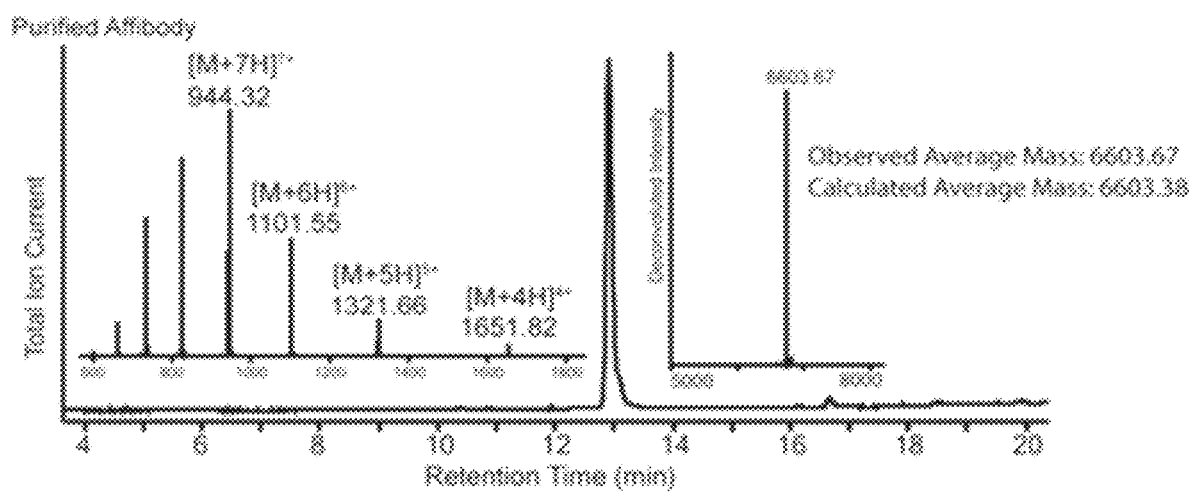
FIG. 9E is, according to certain embodiments, a chromatogram and mass spectrum for the purified affibody.

Using the modified coupling conditions for cysteine, the conotoxin variant and a fragment of the HIV-1 protease peptides were prepared on a 0.1 mmol scale. Eighty nine milligrams (53%) of the crude conotoxin and 90 mg (43%) of the crude HIV-I protease fragment were isolated. To explore the utility of the flow platform in the preparation of synthetic proteins, a 58 residue tri-helical protein based on the Z domain of protein A (referred to as the affibody) was prepared. The synthetic strategy, which can be seen in FIG. 7A, used peptide-hydrazides as thioester precursors for use in native chemical ligation. Peptide hydrazides can be oxidized with $NaNO_2$ to form a C-terminal peptide-azide, which can react with a thiol to form a peptide thioester. The LCMS data for the crude synthetic peptides are shown in FIGS. 7B-D. Variants of these peptides were also prepared using Boc in-situ neutralization methods and the peptides were found to be of similar crude quality (FIGS. 8A-8F). Retention time shifts are due to different chromatographic conditions. Each peptide for the affibody was purified (FIG. 9), the affibody was then synthesized, and the highly pure, full-length affibody was isolated after purification (FIG. 7E).

Although it was possible to implement this protocol in a batch mode, the flow based platform overcame a number of significant obstacles. First, the completely sealed reactor and a preheat loop were immersed in a temperature controlled bath which allowed reagents to be heated in a consistent and controlled manner immediately before reaching the resin bed. This would be difficult in some batch systems. Second, the use of a low volume reactor (about 2.5 mL) and narrow tubing for delivery of solvents and reagents allowed efficient washing with only 20 mL of solvent. In contrast, batch mode automated and manual syntheses typically use large volumes of solvent (about 70 mL per wash). Third, the flow platform was assembled from common laboratory equipment at low cost without machine or glass shop support. Fourth, high quality peptides were obtained quickly without double coupling, double deprotection, ninhydrin or Kaiser tests, or resin mixing. During the studies with ACP(65-74), no decrease in the Val deletion peptide was observed after double coupling Val and double deprotecting the preceding Gln. These additional steps are often employed in batch mode syntheses. Finally, the flow based SPPS system was capable of being adapted to larger synthetic scales by increasing the diameter of reactor. For example, the reactor diameter was doubled and the resulting reactor used to synthesize ACP(65-74) on a 0.2 mmol scale using exactly the same protocol. Another option for increasing the synthetic scale was to simply increase the reactor length. However, this strategy significantly increased the backpressure, which may pose difficulties during synthesis. The flow based SPPS platform in this example allowed for the rapid Fmoc synthesis of polypeptides. It was found that, under flow at 60° C., amide-bond formation and Fmoc removal were fast (within seconds) and did not improve with increased reaction time. Using the flow based Fmoc system, three affibody segments were able to be synthesized and cleaved in one working day. By contrast, the production of similar peptides using optimized Boc in-situ neutralization methods, with 15 minute cycle times, required more than three days. In addition, the purified peptides were ligated to generate synthetic proteins. This approach allowed for the rapid production of highly pure, moderately sized peptides that were easily ligated to obtain larger fragments.

Example 2

This example describes the determination of the deprotection step time. Real-time monitoring of the effluent with an inline UV-Vis detector allowed the deprotection step to be reduced in length. The rate of Fmoc removal was investigated by monitoring the UV absorbance of the reactor effluent at 304 nm. To determine the minimum treatment time for robust Fmoc removal, the deprotection solution was flowed in at 10 mL/min for 60 seconds, 30 second, 15 seconds, or 6 seconds. Twenty seconds at 10 mL/min was found to be sufficient for complete Fmoc removal. Effective Fmoc removal was also achieved during the 6 second steps.

In developing an Na deprotection protocol, piperidine in DMF was selected as the standard deblocking reagent. A concentration of 50% (v/v) in DMF was selected over the more common 20% (v/v) in DMF because the deprotection solution was diluted as it entered the column. A higher concentration was therefore desirable. The flow rate was set at 10 mL/min (maximum) to reach an effective concentration in the minimum time. To determine the length of the deprotection step, ALF peptide was synthesized with a double deprotection of every residue, and the UV absorbance of the effluent was monitored at 304 nm. Piperidine and DMF did not absorb well at this wavelength, but piperidine-DBF, the deprotection product, did. Therefore, the presence of a second peak after the second deprotection indicated that the initial deprotection was inadequate. No second peak was observed after 60 seconds, 30 seconds, and 15 seconds of deprotection, and only a very small peak was observed after a 6 second initial deprotection. In all cases, the first deprotection was at 10 mL/min, and the second was for one minute at 10 mL/min. Since, Fmoc removal has been reported to be sequence dependent, a final deprotection time of 20 seconds was selected. However, it is believed that the 6 second deprotection step (and even faster deprotection steps) would be suitable for many peptide synthesis processes. Additionally, it is believed that, by increasing the flow rate of the deprotection agent, robust Fmoc removal can be achieved in one second or less.

The double deprotection protocol had to be used to determine deprotection time because it took significantly longer to wash the piperidine-DBF adduct out of the resin than to remove the Na Fmoc group. If the effluent was simply monitored until the absorbance returned to near-baseline, most of the "deprotection" time would have been spent washing the resin with deprotection reagent after the deprotection was complete.

Figure 10:
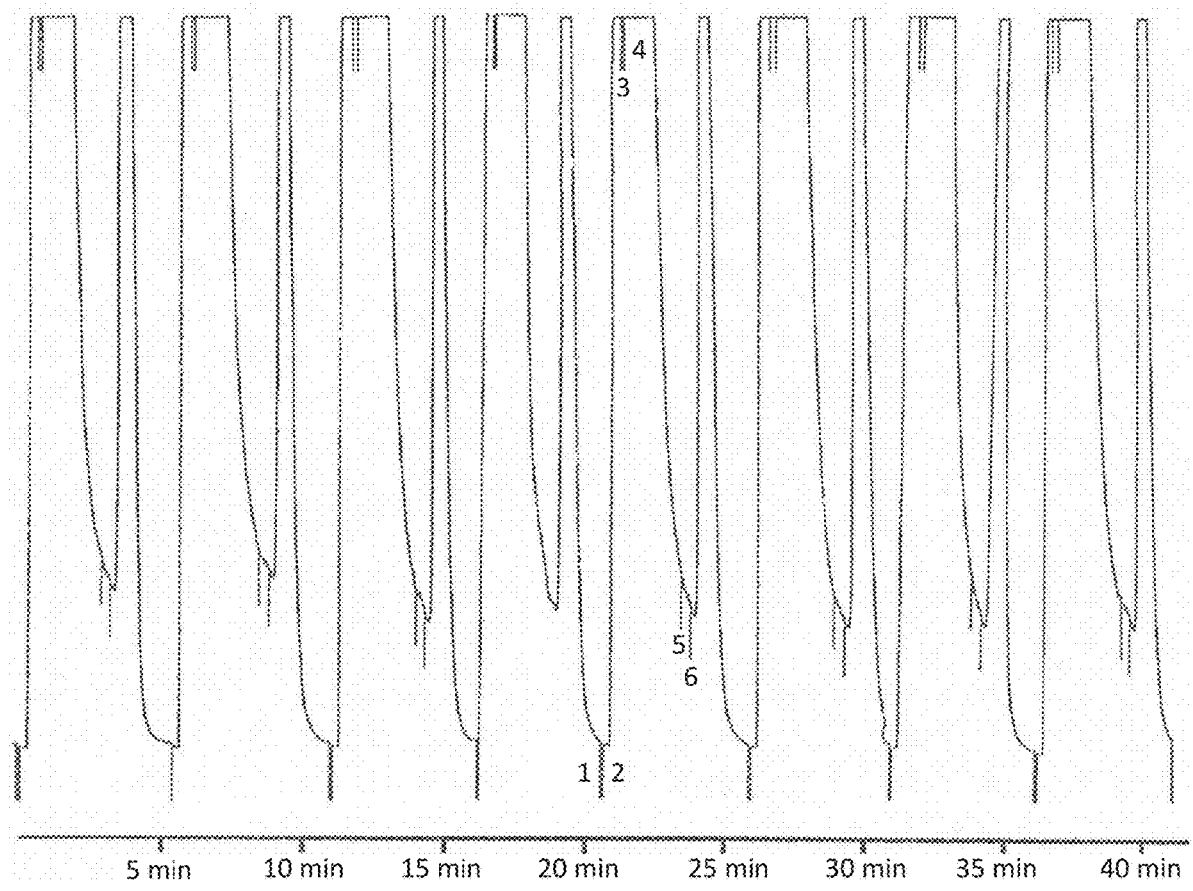
FIG. 10 is a plot of ultraviolet absorbance as a function of time recorded during the synthesis of a peptide, according to one set of embodiments.

FIG. 10 shows the UV record of the incorporation of the final eight residues during the conotoxin synthesis. Negative marks represent manual actions. The scanned trace has been color enhanced and a time-line added, taking zero to be the beginning of the trace. The marks of one cycle have been annotated with 1 indicating the end of the previous wash, 2 indicating the beginning of coupling, 3 indicating the end of coupling, 4 indicating the start of the first wash, 5 indicating the end of the first wash and start of the deprotection, and 6 indicating the end of the deprotection and start of the second wash. The quick connect was moved between 1 and 2, and between 3 and 4. Inconsistencies in cycle time and missing marks were due to human error.

Example 3

This example describes the determination of the wash step time. Real-time monitoring of the effluent with an inline UV-Vis detector allowed the wash step to be reduced in time. The efficiency of the wash step was systematically investigated by monitoring the UV absorbance of the reactor effluent at 304 nm. The time required to wash the amino acid out of the reactor as a function of flow-rate was then investigated. It was determined that the wash efficiency was principally determined by the total volume of solvent used, with about 16 mL of DMF required to remove 99% of the amino acid precursor. However, at flow rates greater than about 6 mL/min, marginally less solvent was required. It was concluded that a 2 minute DMF wash at 10 mL/min was sufficient. Double incorporation of amino acids, which would occur if the DMF wash did not completely remove the amino acid or deprotection solution, was not observed for the 2 minute wash time. Increasing the wash volume did not improve the crude peptide quality. It is believed that even faster wash times could be observed by, for example, increasing flow rate, changing the geometry of the inlet to reduce recirculation, and/or reducing the aspect ratio of the reactor.

Figure 11:
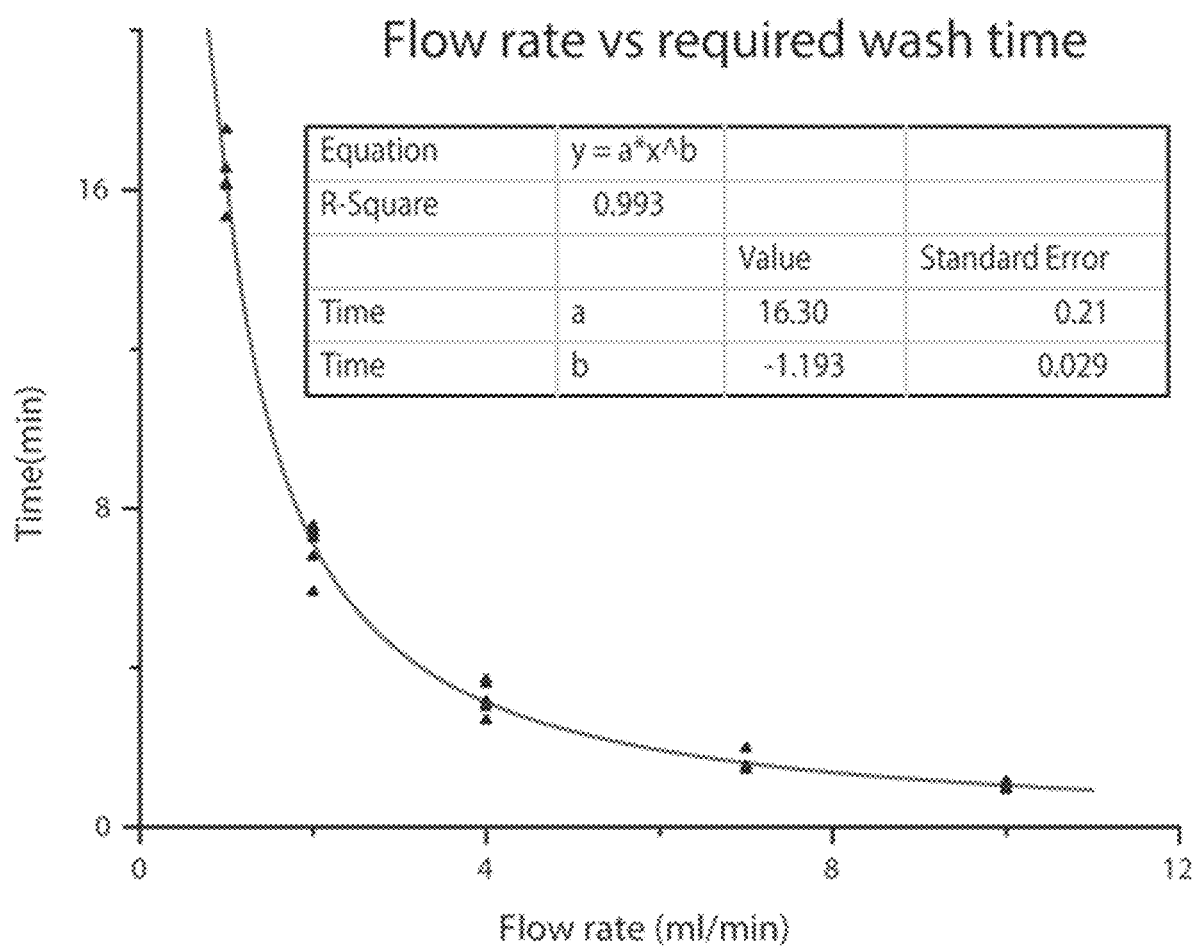
FIG. 11 is a graph of flow rate versus wash time, according to one set of embodiments.

Visual observation of the reactor during wash cycles showed recirculation and mixing of DMF wash solvent and coupling solution. Other solvent exchanges showed the same behavior. Differences in color and refractive indices allowed the direct observation of all exchanges. Based on these observations, it was expected that the wash efficiency was primarily dependent on the volume of solvent used, as predicted by a continuous dilution model. To test this theory, the UV absorbance of the reactor effluent was monitored at 304 nm during the triplicate synthesis of ACP(65-74). During each synthesis, two consecutive residues were washed at 10 mL/min, two at 7 mL/min, two at 4 mL/min, two at 2 mL/min, and the final two at 1 mL/min. Wash rates were randomly assigned to blocks of amino acids, ensuring that no block was washed at the same rate twice. The time required for the detector to desaturate was measured for each residue. Desaturation represents approximately 99% reduction in amino acid concentration. This wash efficiency was selected because the wash was essentially complete, but air and particulate contamination in the detector were less significant than at lower signal levels. The data are shown in FIG. 11. The exponent (parameter b) was significantly below negative one. The value of the exponent meant that less solvent was required to desaturate the detector at higher flow rates. The relationship between desaturation and flow rate was not consistent with the proposed continuous dilution model.

Based on these results, a maximum flow rate (10 mL/min) was selected for the wash. The wash time was set at two minutes, which reliably reduced the final concentration of coupling solution to 0.2% of the initial concentration. This trend is valid with wash rates up to at least 100 ml/min resulting in effective washing observed in 10 seconds. It is believed that even faster washing times could be achieved, for example, by increasing the wash liquid flow rate. No double incorporation, the expected outcome of an inadequate wash, was observed. The apparatus used did not provide a direct way to monitor the removal of piperidine (the UV absorbance is similar to DMF at accessible wavelengths), so the same wash cycle was used for the second wash. If it was assumed that piperidine is removed at the same rate as piperidine-DVB, the two minute wash was an overestimate of the necessary wash time as shown by the UV trace in FIG. 10. The total time of an amino acid addition cycle may be reduced by substantially reducing the washing step.

Example 4

This example describes the determination of minimum coupling time. The effect of coupling time was investigated by synthesizing two model peptides: LYRAG-CONH2 (SEQ ID NO: 2) and Fmoc-ALF-CONH2. For each of five amino acid addition cycles, every amino acid was coupled for a nominal time of 90 seconds, 45 seconds, 30 seconds, 15 seconds, or 7 seconds at 60° C. as shown in FIG. 3. For LYRAG-CONH2 (SEQ ID NO: 2), a significant increase in the Arg deletion peptide was observed when all residues were coupled for 7 seconds. For Fmoc-ALF-CONH2, no significant difference in the quality of the crude product as a function of coupling time was found. Based on these results, a 30 second coupling time was concluded to be sufficient.

It is generally known from the literature that, at room temperature, amide-bond formation is 99% complete in less than 100 seconds using HBTU as a coupling agent. If it was assumed that the reaction rate for this process doubled for every 10° C. increase in temperature, at 60° C. amide bond formation would be completed in about 6 seconds, which would have significantly decreased amino acid addition cycle time. Thus, all subsequent coupling studies were carried out at 60° C. to minimize the cycle time without significantly increasing formation of side products. An important feature of this platform was the ability to simply place the reactor and a preheat loop in a temperature controlled water bath. The preheat loop allowed reagents to be stored at room temperature and then immediately heated before entering the reactor, which allowed the thermal degradation of reagents to be minimized.

LYRAG (SEQ ID NO: 2) was selected as a model peptide to determine the minimum coupling time, because the arginine deletion could be monitored. For 90 seconds, 45 seconds, and 30 seconds nominal coupling times, the coupling solution was delivered at 4, 8, and 12 mL/min, respectively. This flow rate allowed the delivery of 2 mmol of amino acid. Flow rates above 12 mL/min were not reliably obtainable in this system (although other systems could be designed to include higher flow rates), so for the 15 second trial, half of the coupling solution was used (1 mmol amino acid in 2.5 mL 0.4M HBTU in DMF, with 0.5 mL N,N-Diisopropylethylamine (DIEA)). At a coupling time of 7 seconds, the time spent manually moving the quick connect (5-6 seconds) was very significant, so 1.2 mL of coupling solution was delivered. This volume was the volume of the preheat loop, so the coupling solution did not reach the reactor until it was cleared from the lines by the DMF wash. The wash, at 10 mL/min, took 7.2 seconds to clear 1.2 mL, giving a 7 second coupling time. In the other runs, the 5 seconds to move the quick connect was added to the nominal coupling time, as was the time required to deliver about a 10% increase over the nominal volume of coupling solution. The difference in the time taken for the DMF wash solvent and coupling solution to clear the inlet line was subtracted. More accurate coupling times were 93 seconds, 53 seconds, 39 seconds, 23 seconds, and 7 seconds. This does not include the time required to wash the coupling solution from the reactor. The seven second coupling showed increased Arginine deletion, so the 30 second protocol was selected as a conservative estimate. Fmoc-ALF was produced with the same procedure, and showed no change in peptide quality with reduction in coupling time. Data are presented in FIG. 3.

It is believed that using an automated system, using higher flow rates, and using a higher temperature would substantially reduce the coupling time.

Example 5

This example describes the minization of cysteine racemization. The peptides PnIA (A10L) conotoxin, HIV-1 PR(81-99), and GCF were used to explore techniques to minimize cysteine racemization.

In the initial syntheses of PnIA (A10L) conotoxin and HIV-1 PR(81-99), cysteine was activated like all other amino acids (1 eq HBTU, 2.9 eq DIEA), and significant diastereotopic impurities were observed in the products. These were determined to be the result of cysteine racemization. To investigate conditions that reduce racemization, a model system, GCF, was selected because the diasteromer formed upon racemization was resolved by RP-HPLC. The standard synthetic procedure was used, except coupling time was increased to one minute for 60° C. runs and 6 minutes for room temperature (RT) runs. Rink, Gly, and Phe were all activated according to the standard procedure, with one equivalent of HBTU (5 mL, 0.4M) and 2.9 equivalents of DIEA (1 mL). For cysteine, various activation procedures were used as summarized below. For procedures that used less than 1 mL of DIEA, DMF was used to replace this volume. In addition to the activation methods below, an authentic diasteromer was produced using Fmoc-D-Cys (Trt)-OH and the activation procedure of 5. TIC traces are shown for 4, 5, 6, 7 and the authentic diastereomer in FIG. 6. Runs not shown were visually indistinguishable from 4. In all cases, the activator, additive, and 2 mmol amino acid were dissolved in 5 mL DMF, and additional DMF was added as needed. The base was added immediately before use. Reaction 8 employed an isolated C-terminal pentafluorophenyl (Pfp) ester (Fmoc-Cys(Trt)-OPfp) without additional activators, additives, or base. Table 1 summarizes the results, with racemization quantified by integration of the extracted ion current. This enables quantification of racemization below the TIC baseline. The results obtained were consistent with previous reports.

TABLE 1

Reaction conditions and racemization results.

| Reaction | Activator | Additive | Base | Temp | Racemization |
|---|---|---|---|---|---|
| 1 | HBTU (1 eq) | None | DIEA (2.9 eq) | 60° C. | 10% |
| 2 | HBTU (1 eq) | HOBt (1 eq) | DIEA (2.9 eq) | 60° C. | 18% |
| 3 | HBTU (1 eq) | None | DIEA (2.9 eq) | Cys room temp G and F 60° C. | 11% |
| 4 | HBTU (1 eq) | None | DIEA (2.9 eq) | Room temperature | 10% |
| 5 | HBTU (1 eq) | None | DIEA (0.9 eq) | 60° C. | 1% |
| 6 | HBTU (1 eq) | HOBt (1 eq) | DIEA (0.9 eq) | 60° C. | 1% |
| 7 | DCC (0.9 eq) | HOBt (1.1 eq) | None | 60° C. | 1% |
| 8 | OPfp | None | None | 60° C. | 1% |

FIGS. 6A-6E shows GCF produced with various cysteine activation schemes. The peak eluting between the desired product and diastereomer in A and B was hydrolysis of the C-terminal carboxamide. The diastereomer was barely visible. Conditions are listed in table 1. The conditions in FIG. 6A-D show chromatograms for reactions (a) 5, (b) 7, (c) 8, (d) 4, and the (e) the authentic Gly-D-Cys-L-Phe. The total ion current is displayed in each chromatogram.

Example 6

This example describes the synthesis of an affibody. Throughout this section, ligation buffer refers to a 6M GnHCl, 0.2M Sodium Phosphate buffer at the specified pH; buffer P is a 20 mM Tris, 150 mM NaCl solution at pH=7.5.

Oxidation chemistry was used to ligate three fragments into a synthetic, 58 residue protein. Thiozolidine was found to be unstable in the conditions used, so 9.6 mg of fragment Thz-[28-39]-CONHNH$_2$ was converted to a free N-terminal cysteine by treatment with 83 mg methoxyamine hydrochloride in 5 mL of ligation buffer at pH=4 overnight. Quantitative conversion was observed. The N-to-C assembly shown in FIG. 5A was employed instead of the C-to-N synthesis used when thioesters are accessed directly. Fragment [1-27]-CONHNH$_2$ was oxidized to the C-terminal azide by dropwise addition of 0.1 mL of 200 mM aqueous NaNO$_2$ to a solution of 11 mg purified fragment [1-27] CONHNH$_2$ in 1 mL ligation buffer at pH=3 and 0° C. The reaction proceeded for 20 minutes at 0° C., and was then quenched by the addition of 172 mg 4-mercaptophenylacetic acid (MPAA) and 34 mg tris(2-carboxyethyl)phosphine.HCl (TCEP.HCl) dissolved in 4.4 mL ligation buffer (pH=7, room temperature (RT)). To the resulting thioester, 3.4 mL of the crude methoxyamine treated fragment Thz-[28-39]-CONHNH$_2$ were added. After a two hour RT ligation, one half of the crude reaction mixture was purified by RP-HPLC, with 2 mg of highly pure material recovered. Of this, 0.6 mg were oxidized by dissolution in 0.1 mL of ligation buffer and dropwise addition of 0.01 mL of 200 mM aqueous NaNO$_2$ at 0° C. The reaction proceeded for 26 minutes, and was then quenched by addition of 3.1 mg MPAA and 0.78 mg TCEP.HCl dissolved in 0.1 mL ligation buffer (pH=7, RT). The pH was adjusted to 7 and 0.3 mg of fragment Cys-[40-58]-CONH$_2$ were added to the reaction mixture. After a two hour RT ligation, the mixture was diluted with 0.21 mL buffer P, then a further 0.63 mL buffer P to fold the resulting affibody. The crude mixture was concentrated over a 3 kDa membrane to a final volume of 0.075 mL. The crude, folded protein was diluted with 36 mg TCEP.HCl in 3 mL buffer P and purified to homogeneity (FIG. 9).

FIGS. 9A-9E show LC-MS chromatograms of the purified affibody synthesis intermediates and final product. FIGS. 9A-9E are chromatograms of (a) fragment [1-27] CONHNH$_2$, (b) fragment Thz-[28-39]-CONHNH$_2$, (c) fragment Cys-[40-58]-CONH$_2$, (d) ligation fragment [1-39]-CONHNH$_2$, and (e) the final affibody.

Comparative Example 6

This example describes the synthesis of an affibody using a conventional manual Boc in-situ neutralization methods.

Comparable affibody fragments using manual Boc in-situ neutralization methods were synthesized. LC-MS data for these crude peptides is shown in FIGS. 8A-8F, next to the crude peptides synthesized on the flow based SPPS. In all cases, the quality was comparable. Retention time shifts are due to a change in chromatographic conditions.

Example 7

This example describes the design of the system used to for flow based SPPS. Throughout this example the system is referred to as the synthesizer. A schematic of the synthesizer is shown in FIG. 2A. An HPLC pump was used to deliver either methanol purge solvent for washing the pump heads, reactor, and UV detetctor after use, DMF wash solvent for removal of reagents and byproducts during synthesis; or 50% (v/v) piperidine in DMF for deprotection of the N-terminus. The positions of valves 1 and 2 determined which fluid was delivered. A syringe pump was used to deliver coupling solution. To switch between the syringe pump and HPLC pump, a quick connect was manually moved from the outlet of the HPLC pump to the syringe on the syringe pump. A valve would have been generally ineffective because the line between the syringe pump and valve would retain coupling solution, causing incorrect incorporation in the next cycle. The column and a 1.2 mL preheat loop (not shown) were submerged in a water bath to maintain a constant 60° C. Valves 3 and 4 selected a high pressure bypass loop used to clear the UV detector when it was clogged with precipitates, such as the urea byproduct of DCC activation encountered during cysteine racemization studies. The loop was also used to purge the detector without the column in line.

A Varian Prostar 210 HPLC pump, KD Scientific KDS200 syringe pump, Varian Prostar 320 UV detector set to 304 nm, Amersham Pharmacia Biotech chart recorder, and VWR 39032-214 water bath were used in the synthesizer. The HPLC pump delivered about 95% of the nominal flow rate. Disposable 10 mL syringes (BD 309604) were used to deliver coupling solutions. Valve 1 was a Swagelok ⅛" 3-way valve (55-41GXS2). The other valves in the system were Swagelok 1/16" 3-way valves (SS-41GXS1). The methanol, DMF, and 50% (v/v) piperidine lines through valve 1 up to valve 2 were ⅛" OD, 1/16" ID FEP (Idex 1521). The line between valve 3 and 4 was 1/16" OD, 0.010" ID peek (Idex 1531). All other lines were 1/16" OD, 0.030" ID PFA (Idex 1514L). To attach the ⅛" wash and deprotect lines to the 1/16" inlets of valve 2, Swagelok ⅛" to 1/16" (SS-200-6-1) reducing unions were used, followed by a short section of 1/16" tubing. All lengths were minimal, except the tubing between the quick connect and the reactor. This included a 2.6 m (1.2 mL) coil which was submerged along with the reactor and served as a preheating loop to ensure that reactants were at 60° C. before reaching the reactor. Whenever tubing had to be joined, Swagelok 1/16" unions were used (SS-100-6). These were used to attach the preheat loop, join the outlet of the column to a line from valve 4, and repair a severed bypass loop. The manually changed quick connect was a female luer to 10-32 female HPLC fitting (Idex P-659). This connected directly to the syringes on the syringe pump or to a mating male luer to 10-32 female fitting on the line from valve 3 (Idex P-656). The connection between the UV detector and chart recorder was a data link (three 18ga insulated copper wires).

FIG. 2B shows the reactor assembly. The reactor consisted of a tube with standard compression fittings on each end (⅜" to 1/16" reducing unions). On the downstream end there was also a frit. This was positioned by a support designed to fit inside the reactor and seat against the bottom of the fitting on that end. Various frit porosities were used. The part number below was for a 20 micron frit, the most commonly used. The body was a 3.5 inch segment of PFA tubing with outer diameter ⅜" and inner diameter ¼". The frit was a ¼ "sintered stainless steel disk 1/16" thick. The frit support was a 0.5" length of ¼" OD PTFE tubing. As the fittings were tightened, the nut compressed the ferrule against the fitting body, sealing the reactor body to the fitting body. This also compressed the reactor body against the frit, forming an internal seal against the frit. The reactor body and frit were purchased from McMaster-Carr as part numbers S1805K73 and 94461314, respectively. The nut, ferrule, and fitting body are available as a set with the 1/16" nut and ferrule from Swagelok as part number SS-600-6-1. Replacement ferrules are available as SS-600-SET. The reactor was assembled by first cutting the body and frit support to length, ensuring the ends were square. A sharp razor blade and steady hand were used for these operations. Next, the outlet (downstream) end was assembled. The frit was placed on a solid, clean surface and the reactor body was pressed onto it. After verifying that the frit was square and flush with the end of the reactor, the frit support was pushed in slightly, pushing the frit up towards its final position. Firmly seating the reactor body in the fitting body forced the frit to its final position. It was verified that the frit was square and properly positioned under the ferrule, then the fitting was installed according to the manufacturer's instructions. Once sealed, the frit could not be removed and reseated. Finally, the inlet fitting was installed according to the manufacturer's instructions. A high pressure reactor with a stainless steel body was also built. In this case, the downstream fitting had to be tightened well beyond specification to effect a seal with the frit. The reactor was typically replaced every 3-8 syntheses. When replacing the reactor, the ferrules, frit and reactor body were not reused. All other parts were reused. The nuts were recovered by cutting the reactor body in half.

To load the reactor, the upstream fitting body was removed and a slurry of resin in methanol was pipetted in. The reactor was completely filled with methanol, and the fitting body was reinstalled. The inlet line and preheat loop were filled with solvent by attaching them to the quick connect and running the HPLC pump before attaching them to the reactor. The reactor was then kept upright in the water bath so that any small bubble would move to the top and not interfere with wetting the resin. Before the first coupling, the resin was washed for two minutes with DMF at 10 ml/min.

Example 8

This example describes the design of a large scale reactor for use in flow based SPPS. FIG. 12 shows the larger reactor. The design principles of the small scale reactor used for all syntheses translated directly to larger scales. In order to preserve the same cycles, however, the volume of the reactor had to be constant. Two problems were encountered when scaling up four times to a ⅝" OD, ½" ID tube. First, there were no standard ⅝" to 1/16" compression fittings. Second, the minimum distance between ⅝" fittings is quite large, meaning there is a large minimum volume. To overcome the first problem, a ⅝" to ⅜" fitting followed by a ⅜" to 1/16" fitting was used, but this necessitated a joining length of ⅜" tubing that greatly increased the already large volume of the reactor.

To reduce the reactor volume, a 316SS insert was machined that consisted of a nominal ½" OD segment followed by a ⅜" OD segment with a ¼" through hole. A ⅝" to ⅜" reducing union was bored out to give a ⅜" through hole, the insert was seated, and the ⅜" ferrule swaged on. After this, the insert could not be separated from the fitting. When installed, the ½" part of this insert-fitting sat in top of the reactor and limited the volume.

This was effective, but there was still a large volume from the ¼" hole. This volume was reduced by inserting a ¼" OD, ⅛" ID PFA tube and cutting it flush. To further reduce the volume, a ⅛" OD, 1/16" ID PFA tube was inserted by heating and drawing a section of tubing to a narrower diameter, threading it through, and pulling until all tubing in the insert was of the proper diameter. Both sides of the tube were cut flush and the drawn section was discarded. A ⅜" to 1/16" reducing union was installed on the open end of the ⅜" segment to interface with the rest of the system. This insert-fitting is pictured in FIG. 12A (left). To prevent the upstream insert fitting from becoming permanently sealed into the tube like the frit, the nominal ½" segment was machined to 0.496" and polished.

Figure 12A:
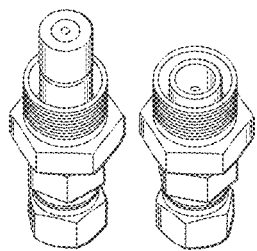
FIG. 12A is, according to one set of embodiments, a photograph of an inlet (left) and outlet (right)

A similar piece was machined for the outlet side, with a ½" section the proper length to seat the frit under the ferrule. To prevent all of the solvent from being forced through a small central section of the frit, a ⅜" step 0.05" deep was cut. The bottom of this hole tapered to a ⅛" through hole at 31 degrees from horizontal (a standard drill bit taper). A ⅛" OD, 1/16" ID PFA tube was inserted to further limit the volume. This piece positioned the frit and sat largely below the ferrule, so a standard finish was adequate. The one pictured in FIG. 12A is PTFE, and was installed in a bored through ⅝" to ⅜" reducing union in exactly the same way as the upstream insert. A ⅜" to 1/16" reducing union was installed on the open end of the ⅜" segment to interface with the rest of the system.

Tubing was used to limit the internal volume, rather than directly making a small hole, to simplify fabrication.

Figure 12B:
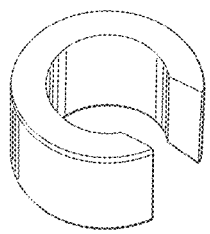
FIG. 12B is, according to one set of embodiments, a photograph of a spacer.
Figure 12C:
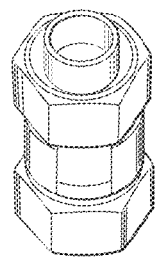
FIG. 12C is, according to one set of embodiments, a photograph of a reactor body unit.
Figure 12D:
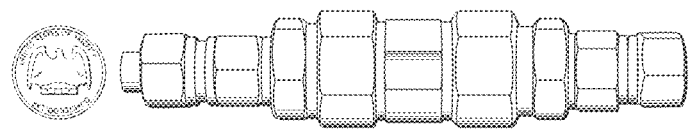
FIG. 12D is, according to one set of embodiments, a photograph of an assembled reactor.
Figure 12E:
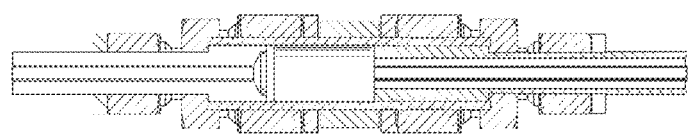
FIG. 12E is, according to one set of embodiments, a schematic of the reactor showing the reactor body, frit, and spacer.

To assemble the reactor, the frit was pressed in and the downstream insert-fitting installed as a regular fitting. The upstream insert-fitting was then installed as a regular fitting. Despite cutting it undersize and polishing, the upstream inset-fitting was very tight and difficult to remove. For subsequent reactors, an aluminum spacer was used so that the nut could not move down, and would instead eject the insert-fitting when loosened. A vertical window was added to the spacer to maintain adequate optical access. The spacer sets the internal volume to 2 mL and enables reproducible production of reactors. A picture of the assembled large reactor is shown in FIGS. 12B, 12D, and 12E.

Example 9

This example describes the techniques used to reduce pressure in the reactor. Pressure drop was inherently caused by the resin. Pressure drop was overcome by employing a rest period after high pressure flows or using a large reactor.

A low pressure polymer reactor was used, so an overpressure alarm on the HPLC pump was set to shut off the pump at 240 psi, which was occasionally triggered. When the alarm was triggered, the system was allowed to rest for 30 seconds, and the pumps were restarted without further incident. During this resting phase, the resin visibly expanded. By observing the HPLC pump pressure, it was concluded that if too much pressure was applied to the beads, they begin to compact. This increased the pressure drop across the bed, and the rate of compaction, which quickly triggers the over pressure alarm. Similar 1% divinyl benzene crosslinked polystyrene resin available for gel permeation chromatography from Bio-Rad was recommended for gravity driven separations only, because it is very soft once swollen.

When the reactor was disassembled immediately after such an event, the resin looked like a solid block and, when probed with a pipette tip, felt like a hard mass. It was difficult to immediately pipette it out. After a few tens of seconds, the resin relaxed and could be pipetted out. A high pressure stainless steel reactor was built and tested, but the very high pressure necessary to maintain a high flow through a compacted bed (>1000 psi) was reminiscent of previous continuous flow SPPS that struggled with extrusion of the resin through the frit.

It was believed that the initial compaction took place at the boundary of the frit and the resin, such that the resin was able to mechanically block the pores of a course frit with relatively little deformation. To test this theory, the original 40 micron frit was replaced with a 20 micron frit, and, in more limited trials, 10 micron frits and 2 micron frits. Smaller pores did not eliminate the problem, but seemed to qualitatively reduce its severity. From this it was concluded that the problem was inherent in the resin, and can only be eliminated by running at lower flow rates or reducing the bed height (using smaller scales and/or larger reactors).

The use of harder, more highly crosslinked resin has been reported, but the resulting peptides were of inferior quality. The solution used here was to wait 30 seconds following a high pressure event. This was effective and expedient, allowing progress on a reasonable scale without further optimizing the dimensions of the reactor. A limited number of trials with a ½" ID reactor (described in Example 8) show no overpressure with up to 200 mg of resin, operating on the same cycle.

Example 10

This example describes the preparation of ALFALFA-CONHNH$_2$ (SEQ ID NO: 18) in six minutes. A high capacity pump head for the HPLC pump used in previous examples was used to deliver 100 ml/min of DMF during the wash step, 100 ml/min of 50% piperidine in DMF during the deprotection step, and 12 ml/min of activated amino acids during the coupling step. The reactor and preheat loop were maintained at 60° C. by immersion in a water bath.

Figure 13:
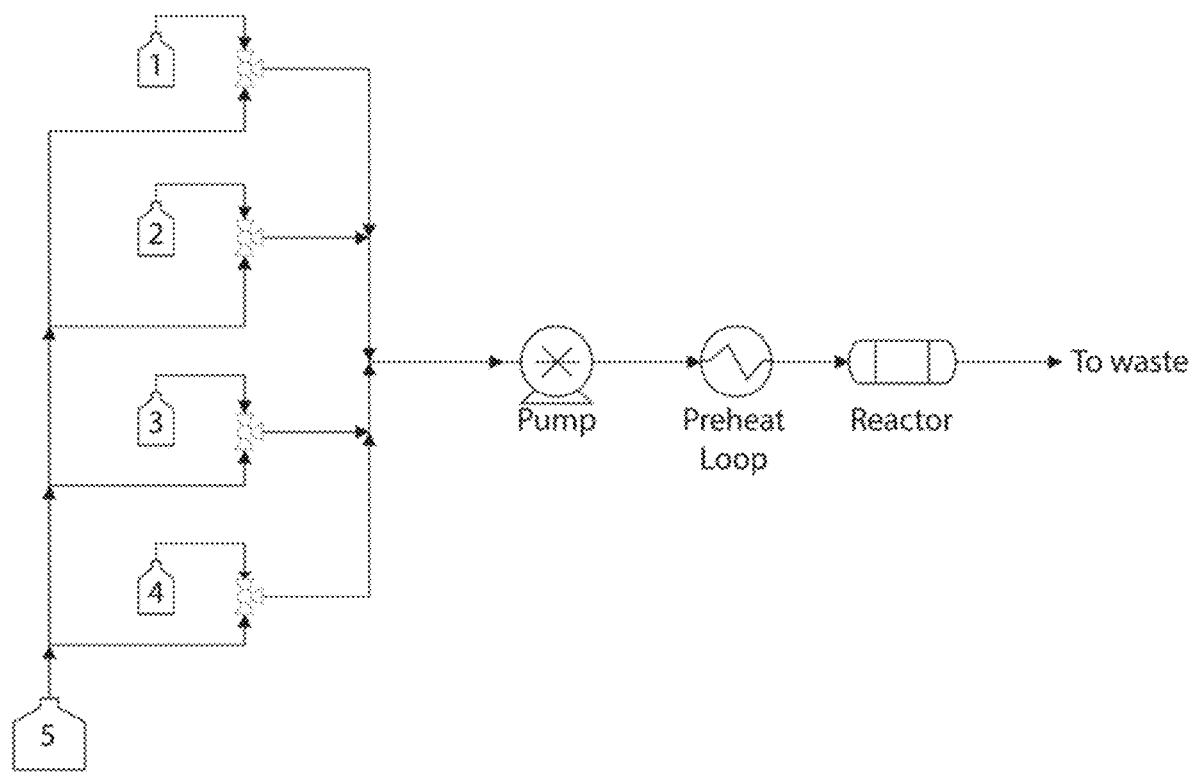
FIG. 13 is a schematic illustration of an exemplary system for performing peptide synthesis, according to one set of embodiments.

The apparatus shown in FIG. 13 was constructed. Reservoir 1 contained activated alanine, reservoir 2 contained activated leucine, reservoir three contained activated phenylalanine, reservoir 4 contained 50% piperidine in DMF, and reservoir 5 contained DMF. Each activated amino acid was prepared by combining 50 ml of 0.4M HBTU in DMF with 20 mmol Fmoc protected amino acid. Immediately before the start of the run, 10 mL of DIEA was added to each of the amino acid reservoirs. To obtain the desired flow rates, 1.5 bars of nitrogen head pressure was applied to each reservoir. All tubing upstream of the pump was ⅛" OD, 1/16" ID PFA. The three way valves were Swagelok ⅛" three way valves. The common lines of three way valves were routed into a switching valve (Valco C25-6180) which selected between the reagents. All valves were manually controlled. The pump was a Varian Prostar 210 with a 100 ml/min pump head. The preheat loop was 1.8 m of 1/16" OD, 0.030" ID PFA tubing. The reactor used was the larger reactor shown in FIG. 12 and described in Example 8. The reactor contained 120 mg of chlorotrityl hydrazide functionalized polystyrene resin, prepared from commercial chlorotrityl chloride resin using standard methods known to those of ordinary skill in the art. Using the larger reactor helped in maintaining a manageable pressure drop at 100 ml/min.

Figure 14:
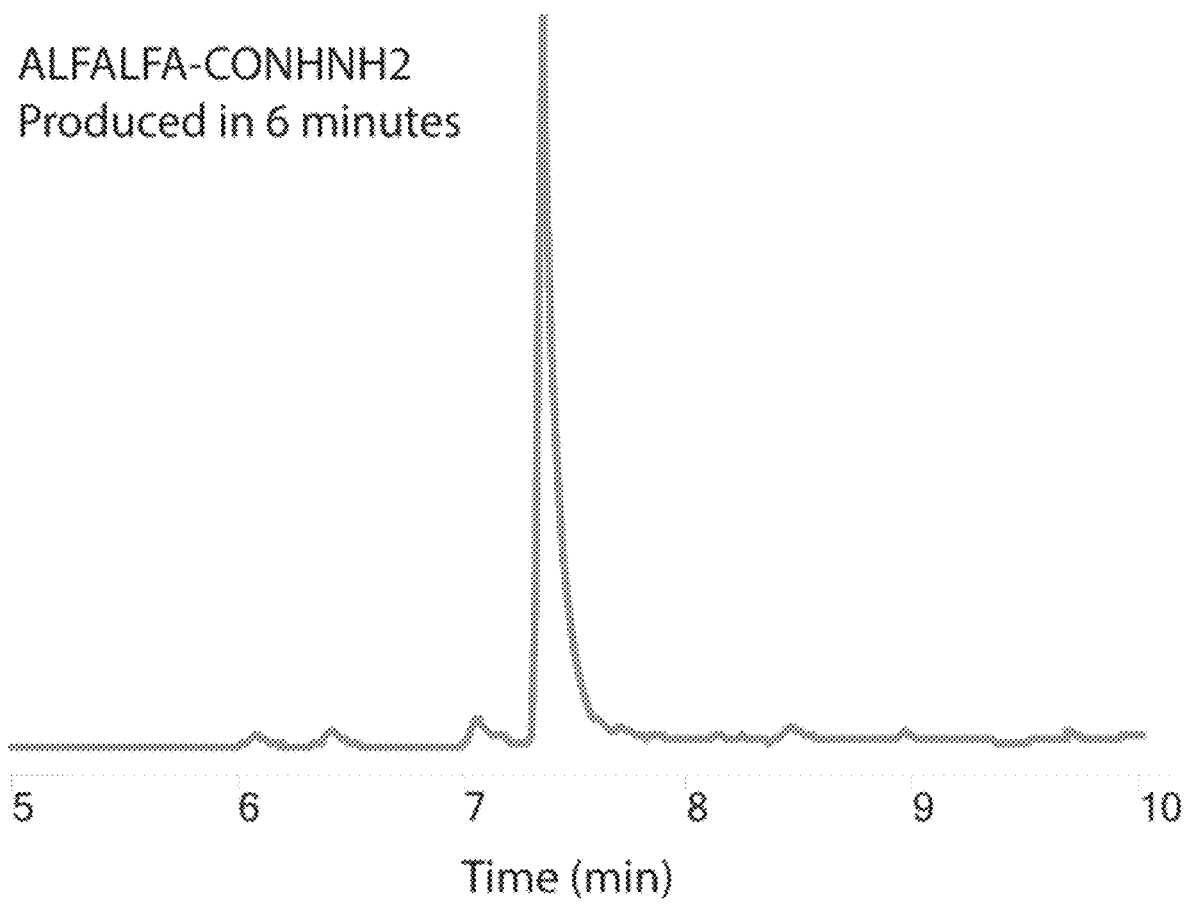
FIG. 14 is, according to certain embodiments, an exemplary total ion chromatogram of a synthesized peptide ALFALFA-CONHNH$_2$ (SEQ ID NO: 18)

One synthetic cycle was performed as follows. First a 20 second coupling was performed at 12 ml/min. The multiport valve was set to the desired amino acid and the three way valve was set to DMF. All other three way valves were set to DMF. After thirty seconds, the selected three way valve was switched from amino acid to DMF and the pump flow rate was set to 100 ml/min. After five seconds, the multiport valve was switched to piperidine. After another five seconds, the selected three way valve was switched from DMF to piperidine. After 10 seconds the selected three way valve was switched back to DMF. After five seconds, the multiport valve was moved to the next desired amino acid. After another five seconds, the flow rate was reduced to 12 ml/min and the selected three way valve was switch from DMF to the next desired amino acid, starting the next cycle. The total time for each step was as follows: 20 second coupling, 10 second wash, 10 second deprotection, and 10 second wash. The total time for each cycle was 50 seconds. The total ion chromatogram from the LC-MS analysis of the crude material is shown in FIG. 14.

All of the above-listed times are believed to be conservative estimates of what would be required to achieve 99%+ yields. It is now known that at a flow rate of 20 ml/min the deprotection is finished in 5 seconds, and it is expected that at 100 ml/min the deprotection requires substantially less than 5 seconds. Longer peptides, such as the common model peptide ACP(65-74), could be prepared, for example, by integrating additional 3-way valves. The general strategy described in this example is expected to be viable for the production of any peptide, including those produced using the cycles described in Example 1.

Example 11

This example describes an improved synthesis scheme, in which the synthesis times (relative to Example 1) were substantially reduced. The cycle time for the synthesis in this example was less than 3 minutes. To reduce the cycle time relative to Example 1, the wash step was adjusted. All tubing upstream of the pump was replaced with ⅛" OD 1/16" ID PFA, and the two valves upstream of the pump were replaced with ⅛" Swagelok three way valves. All tubing lengths were minimal. All other system components were substantially unchanged relative to Example 1. Unless explicitly mentioned below, all procedures remained the same, relative to Example 1.

The larger tubing and a high capacity pump head (maximum 50 ml/min) were used to deliver DMF and deprotection reagent at 20 ml/min. As expected based on FIG. 11, a one minute wash at 20 ml/min proved to be adequate in all cases. Furthermore, a 5 second deprotection step was found to be adequate at these flow rates. The coupling step was unchanged. This yielded a total cycle time of 2 minutes 35 seconds to about 2 minutes and 50 seconds, depending on the speed with which the manual steps are performed. The wash was set at 20 ml/min instead of the maximal 50 ml/min because most users have difficulty manually operating the system at the higher flow rate. It is expected that automation can be used to overcome this human limitation and allow for the implementation of cycles of about 10 seconds per residue with sufficiently large pumps.

Figure 15:
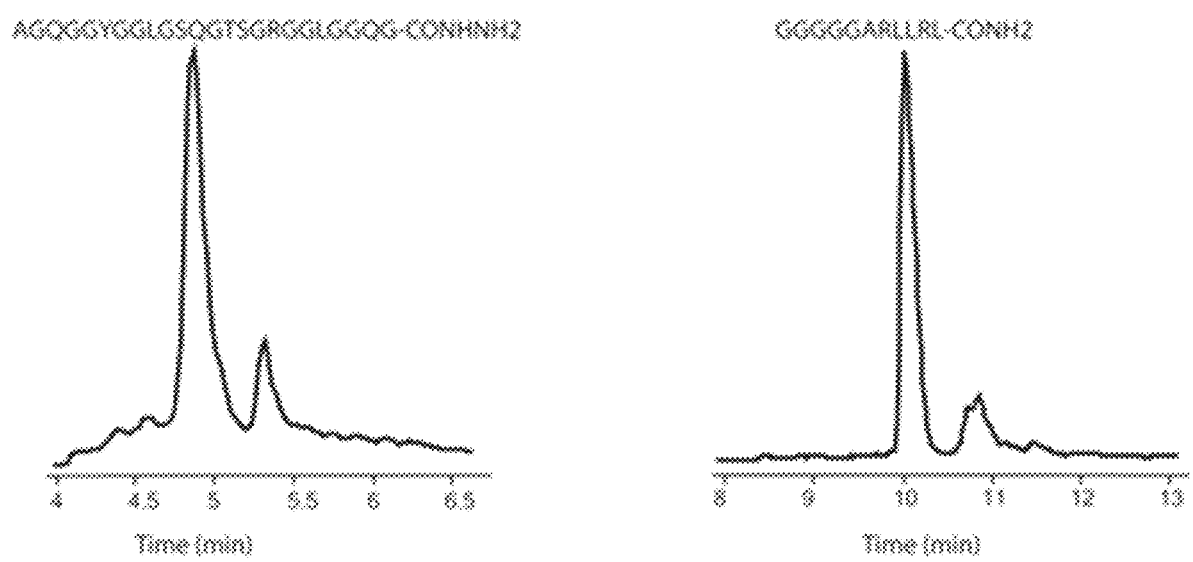
FIG. 15 shows two exemplary chromatograms of peptides made using certain of the protein synthesis systems described herein (sequences from left to right correspond to SEQ ID NOs.: 16 to 17, respectively).

Two chromatograms of peptides made using this cycle are shown in FIG. 15. In each case the main peak is the desired product. These are typical results for peptides of this length.

Example 12

This example describes in more detail the materials and methods used in Examples 1-11.

2-(1H-Benzotriazol-1-yl)-1,1,3,3-tetramethyluronium hexafluorophosphate (HBTU), 2-(7-Aza-1Hbenzotriazole-1-yl)-1,1,3,3-tetramethyluronium hexafluorophosphate (HATU), hydroxybenzotriazole (HOBT), and Na-Fmoc protected amino acids were from Chem-Impex International, IL, NovaBioChem, Darmstadt, Germany, and Peptide Institute, Japan. 4-methylbenzhydrylamine functionalized cross-linked polystyrene (MBHA resin) and p-Benzyloxybenzyl alcohol functionalized crosslinked polystyrene (Wang resin) were from Anaspec, Calif. N,N-Dimethylformamide (DMF), dichloromethane (DCM), diethyl ether, methanol (MeOH) and HPLC-grade acetonitrile were from VWR, PA. Triisopropyl silane (TIPS) and 1,2 Ethanedithiol were from Alfa Aeser, MA. Trifluoroacetic acid (TFA) was purchased from NuGenTec, CA and Halocarbon, NJ. Solvents for LC-MS were purchased from TJ Baker and Fluka. All other reagents were purchased from Sigma-Aldrich, MO.

Common solvent mixtures used throughout these experiments were: 0.1% (v/v) TFA in water (A), 0.1% (v/v) Formic acid in water (A'), 0.1% (v/v) TFA in acetonitrile (B), and 0.1% (v/v) formic acid in acetonitrile (B').

Figure 4A:
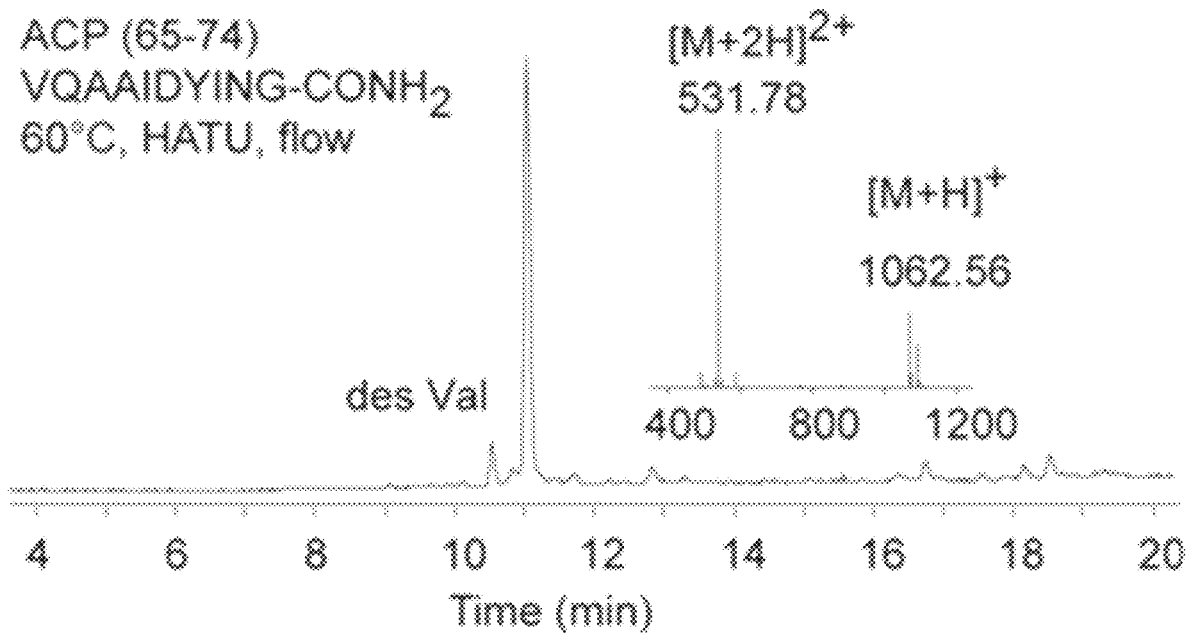
FIG. 4A is, according to certain embodiments, a chromatogram and mass spectrum for ACP (65-74) peptides (SEQ ID NO: 3) synthesized using HATU.
Figure 4B:
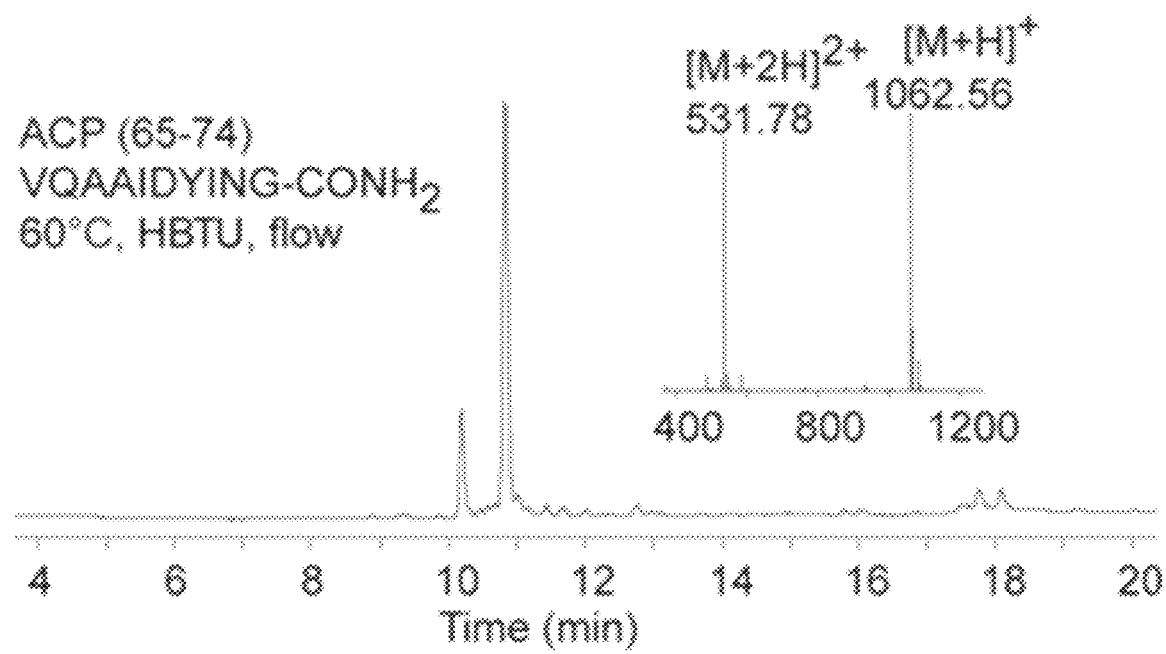
FIG. 4B is, according to certain embodiments, a chromatogram and mass spectrum for ACP (65-74) peptides (SEQ ID NO: 3) synthesized using HBTU.
Figure 4C:
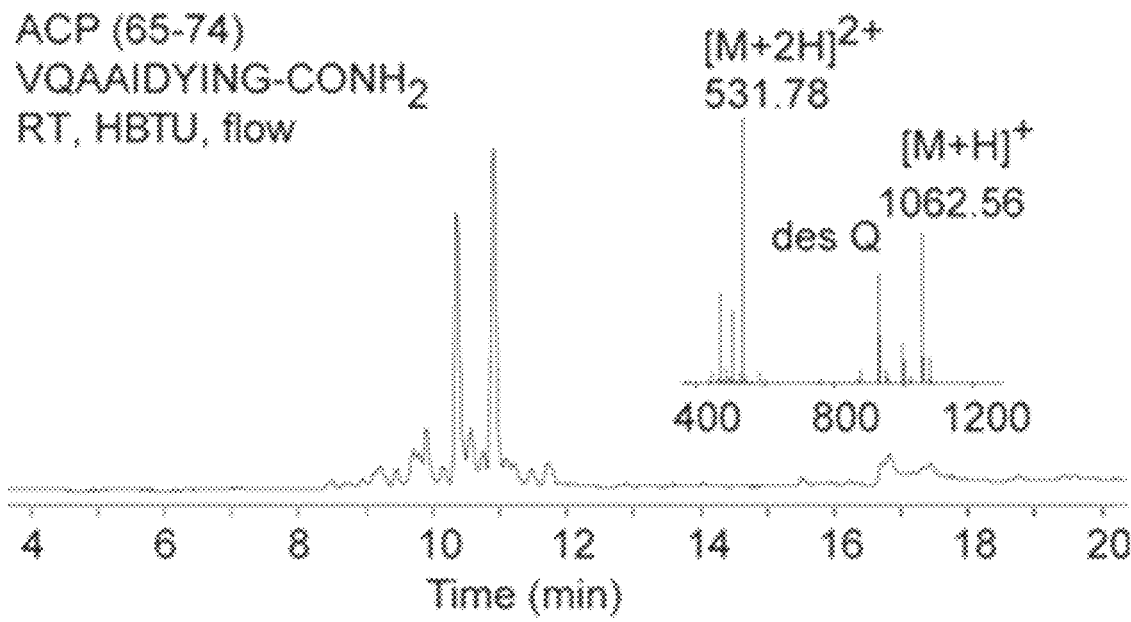
FIG. 4C is, according to certain embodiments, a chromatogram and mass spectrum for ACP (65-74) peptides (SEQ ID NO: 3) synthesized under batch conditions.
Figure 4D:
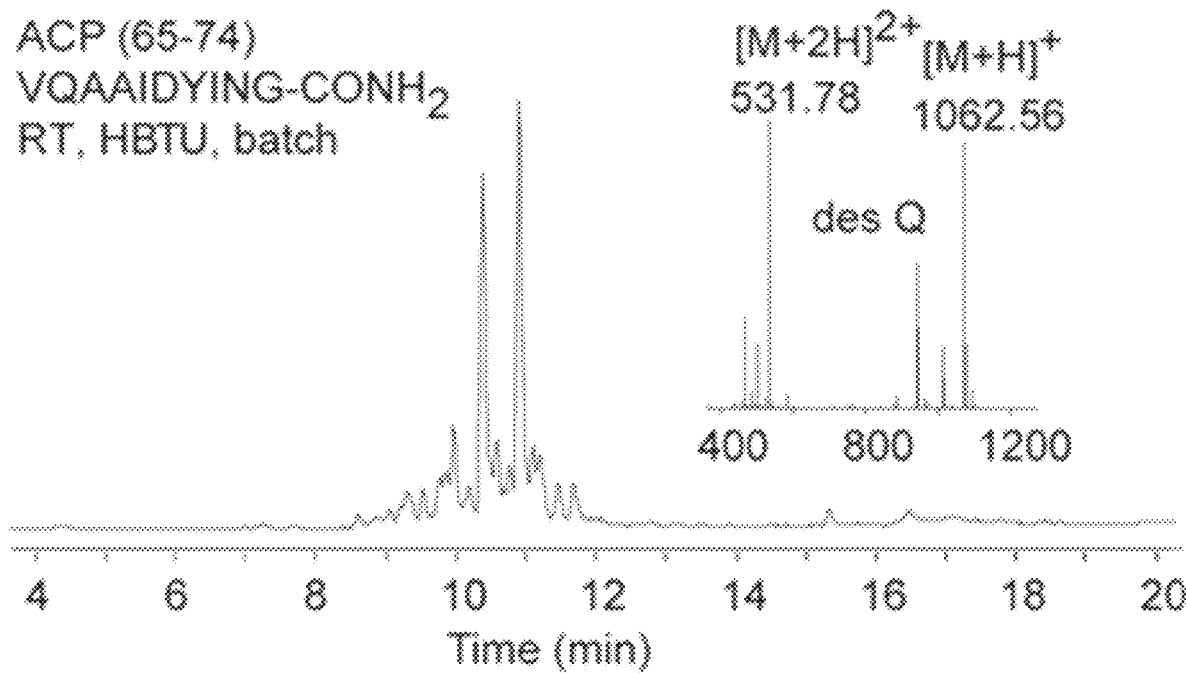
FIG. 4D is, according to certain embodiments, a chromatogram and mass spectrum for ACP (65-74) peptides (SEQ ID NO: 3) synthesized under flow conditions.
Figure 6A:
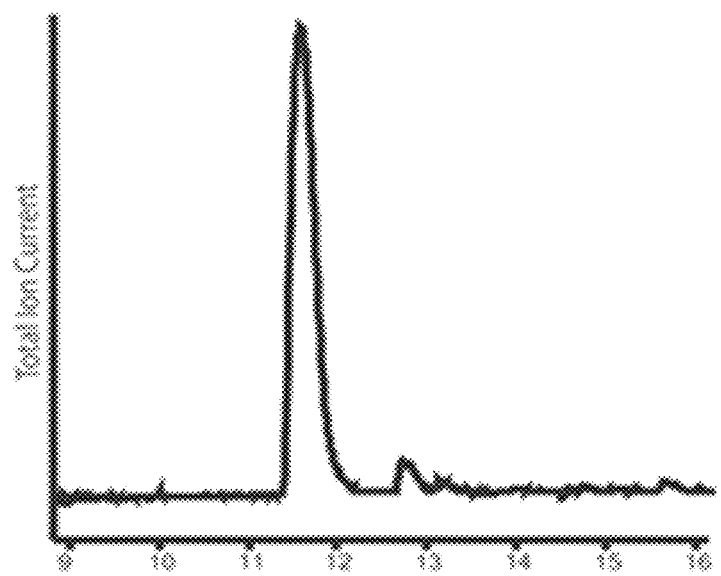
FIG. 6A is, according to certain embodiments, a total ion current chromatograph for GCF peptide synthesized under conditions 5, as shown in Table 1.
Figure 6B:
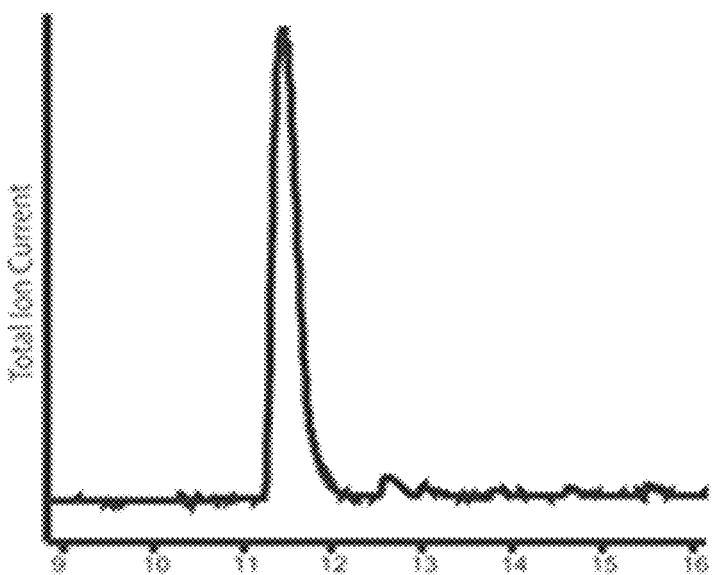
FIG. 6B is, according to certain embodiments, a total ion current chromatograph for GCF peptide synthesized under conditions 7, as shown in Table 1.
Figure 6C:
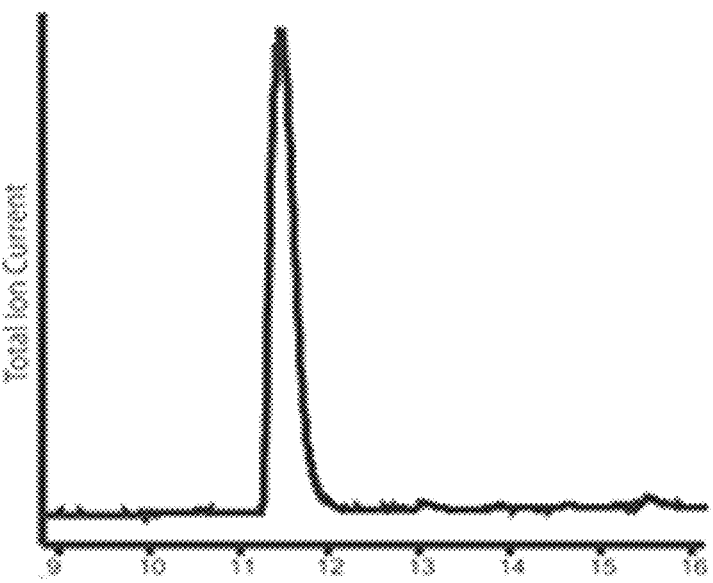
FIG. 6C is, according to certain embodiments, a total ion current chromatograph for GCF peptide synthesized under conditions 8, as shown in Table 1.
Figure 6D:
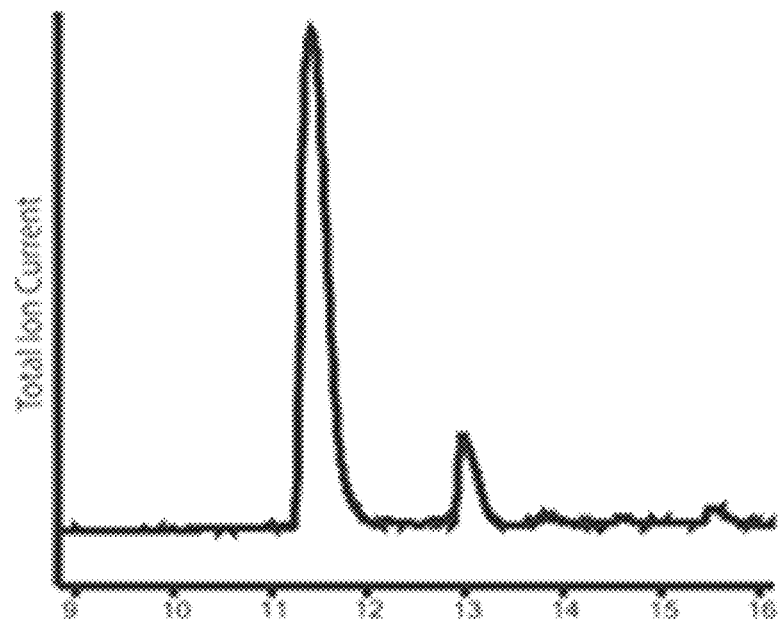
FIG. 6D is, according to certain embodiments, a total ion current chromatograph for GCF peptide synthesized under conditions 4, as shown Table 1.
Figure 6E:
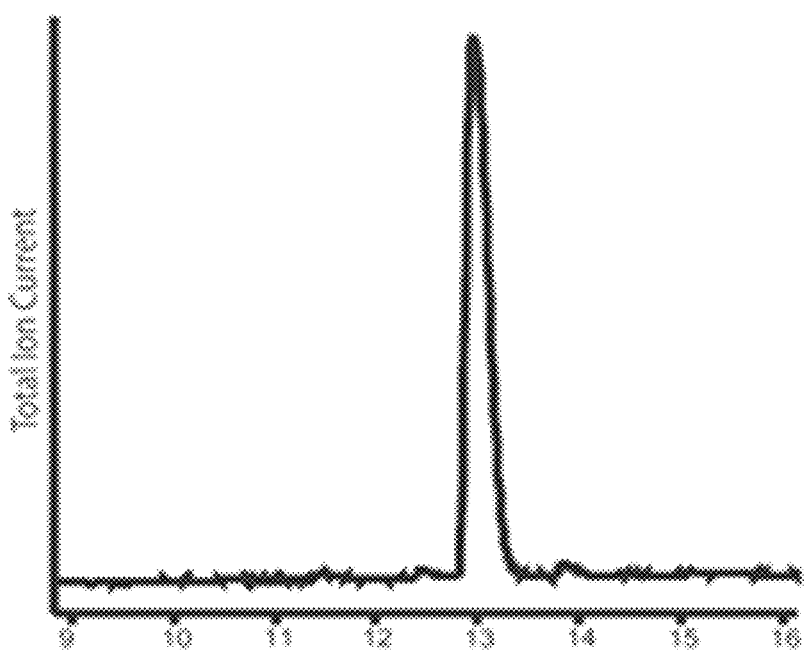
FIG. 6E is, according to certain embodiments, an exemplary total ion current chromatograph for an authentic Gly-D-Cys-L-Phe sample.

All peptides except the ACP(65-74) batch in FIG. 4D were synthesized on the flow based SPPS system. All peptides except ACP(65-74) batch and ACP(65-74) flow RT in FIGS. 4D and 4C were synthesized at 60° C., with reagents preheated immediately before use via a preheat loop (see synthesizer design). One synthetic cycle consisted of an amino acid exposure step (e.g., amide bond formation, also referred to as coupling in the examples), an amino acid removal step (e.g., removal of the coupling reagent, also referred to as a wash step in the examples), a deprotection agent exposure step (e.g., Na Fmoc removal, also referred to as deprotection in the examples), and a deprotection agent removal step (e.g., removal of deprotection reagent and reaction product, piperidine-dibenzofulvene (piperidine-DBF), also referred to as a wash in the examples).

Unless noted, coupling was performed by delivering the following coupling solution at 12 ml/min (for approximately 30 seconds). The activated coupling solution consisted of 2 mmol of Na-Fmoc and side chain protected amino acid dissolved in 5 ml of 0.4M HBTU in DMF and 1 mL of DIEA. Cysteine was dissolved in 5 mL 0.4M HBTU in DMF, 0.687 mL neat DMF, and 0.313 mL DIEA. In both cases, amino acids were dissolved in HBTU solution up to several hours before use, and DIEA was added within two minutes of use. Volumetric measurements were made at RT (20° C.). The ACP(65-74) shown in FIG. 4A was synthesized by substituting HATU for HBTU in the above solution.

Next, the coupling solution was removed with 20 mL of DMF delivered at 10 mL/min over 2 minutes, and then the Na-Fmoc protection group was removed with 3.3 mL of 50% (v/v) piperidine in DMF delivered at 10 mL/min over 20 seconds. Excess piperidine and piperidine-DBF were removed with 20 mL of DMF delivered at 10 ml/min over 2 minutes to complete one cycle.

All peptides were synthesized on 100 mg of 1% divinyl benzene crosslinked polystyrene resin. To produce C-terminal carboxamide peptides, MBHA functionalized resin with a loading of 1 mmol per gram was used, and the first residue coupled was the TFA labile Rink linker. To produce C-terminal hydrazide peptides for ligation, Wang resin, functionalized as below, was used. The loading was 0.6 mmol/g (0.06 mmol scale).

Non-cysteine containing carboxamide peptides were cleaved from the resin and side-chain deprotected by treatment with 2.5% (v/v) water and 2.5% (v/v) TIPS in TFA for two hours. Cysteine containing carboxamide peptides were cleaved from the resin and side chain deprotected with 2.5% (v/v) EDT, 2.5% (v/v) TIPS, and 1% (v/v) water in TFA for two hours. Hydrazide peptides were cleaved with 5% (v/v) EDT, 5% (v/v) TIPS, and 2.5% (v/v) water in TFA for two hours. In all cases, the resin was removed and compressed air was used to evaporate the cleavage solution to dryness at RT. The resulting solids were washed three times with cold diethyl ether, dissolved in 50% A/50% B (v/v), and lyophilized. Side chain protection was as follows: Arg(Pbf), Tyr(tBu), Lys(Boc), Asp(OtBu), Gln(Trt), Ser(tBu), His (Trt), Asn(Trt), Trp(Boc), Glu(OtBu), Thr(tBu), Cys(Trt).

The Wang resin was functionalized as follows: 5.47 g Wang resin was added to a 500 ml round bottom flask and suspended in 98 mL of DCM and 1.12 mL of N-Methyl morpholine. This was stirred in an ice bath for 5 min and 2.03 g p-nitrophenol chloroformate was added as a powder. This mixture was stirred for 8.5 hours. The ice in the bath was not replenished, which allowed the reaction to slowly reach RT. The mixture was filtered and the solids washed with DCM, DMF, MeOH, and DCM to give a white resin. The resulting resin was placed in a clean 500 ml round bottom flask in an ice bath, and suspended in a prepared mixture of 210 mL DMF, 54 mL DCM, and 1.1 mL hydrazine monohydrate prechilled to 0° C. This yielded a bright yellow solution. The reaction proceeded for 18 hours in an ice bath that was allowed to melt. The mixture was then filtered, and the solids washed as before to give hydrazine-functionalized Wang resin.

All peptides were analyzed on an Agilent 6520 Accurate Mass Q-TOF LC-MS. For all peptides except GCF and LYRAG (SEQ ID NO: 2), an Agilent C3 Zorbax SB column (2.1 mm×150 mm, 5 µm packing) was used. The flow rate was 0.4 mL/min of the following gradient: A' with 1% B' for 3 minutes, 1-61% B' ramping linearly over 15 min, and 61% B' for 4 minutes. For GCF and LYRAG (SEQ ID NO: 2), an Agilent C18 Zorbax SB column (2.1 mm×250 mm, 5 µm packing) was used. The flow rate was 0.4 mL/min of the following gradient: A' with 1% B' for 5 minutes, 1-61% B' ramping linearly over 15 min, and 61% B' for 4 minutes.

The peptides were purified as follows. Crude peptides were dissolved in 95% A/5% B (v/v) and purified on a Waters preparative HPLC with an Agilent Zorbax SB C18 column (21.2 mm×250 mm, 7 µm packing), a linear gradient from 5%-45% B in A over 80 min, and a flow rate of 10 mL/min. The crude affibody Fragment 1-39 ligation product was purified on a Beckman System Gold semi-preparative HPLC with a Zorbax C18 column (9.4 mm×250 mm, 5 µm packing), a linear gradient from 10% to 55% B in A over 90 minutes, and a flow rate of 5 mL/min. The final affibody was purified on the same system with the same gradient, using a Jupiter C18 column (4.6 mm×250 mm, 5 µm packing) and a flow rate of 2.3 mL/min.

For all purifications, one minute fractions were collected and screened for the correct mass on a PerSpective Biosystems Voyager-DE MALDI-TOF using 2 µL of the fraction co-crystallized with 2 µL of 50% A'/50% B' (v/v) saturated with alpha-cyano-4-hydroxycinnamic acid matrix. The purity of pooled fractions was confirmed by LC-MS, as above.

The UV detector response was quantified as follows. To understand the UV traces produced and the wash efficiencies they represent, the response of the UV detector was quantified. To determine the approximate concentration of amino acid in the UV traces, a serial dilution of Fmoc-Ala-OH coupling solution was prepared. The initial concentration of amino acid was about 0.3M (2 mmol in 6.5 mL total volume) 10×, 100×, 1000×, 10,000 and 100,000× dilution standards were prepared and injected directly into the UV detector. The 100× dilution ($3 \times 10^{-3}$M) was just below saturation. The 10,000× dilution ($3 \times 10^{-5}$M) standard was just above baseline, about 1% of scale, as expected. The 100,000× dilution was below the detection limit. The highly reproducible washout traces (FIG. 10) show that this is representative of all amino acids (qualitatively different traces between cycles would be expected if the absorbance was vastly different).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A process for adding amino acid residues to peptides, comprising:

flowing a first stream comprising amino acids and a second stream comprising an amino acid activating agent substantially simultaneously such that the first stream and the second stream are merged to form a mixed fluid stream comprising activated amino acids; and flowing the mixed fluid stream into a reactor containing solid support on which peptides have been immobilized such that an activated amino acid is added to at least 99% of the immobilized peptides.

2. The process of claim 1, further comprising performing at least 10 amino acid addition cycles subsequent to flowing the mixed fluid.

3. The process of claim 1, further comprising performing at least 50 amino acid addition cycles subsequent to flowing the mixed fluid.

4. The process of claim 1, further comprising performing at least 100 amino acid addition cycles subsequent to flowing the mixed fluid.

5. The process of claim 1, wherein the flowing is performed such that peptides comprising two or more amino acid residues are added to at least 99% of the immobilized peptides.

6. The process of claim 1, further comprising exposing a deprotection reagent to the immobilized peptides to remove one or more protection groups from at least a portion of the immobilized peptides.

7. The process of claim 6, wherein the one or more protection groups comprise fluorenylmethyloxycarbonyl protection groups.

8. The process of claim 6, wherein the one or more protection groups comprise tert-butyloxycarbonyl protection groups.

9. The process of claim 1, wherein the solid support is contained within a packed column and/or a fluidized bed.

10. The process of claim 1, wherein the solid support comprises polystyrene and/or polyethylene glycol.

11. The process of claim 1, wherein the solid support comprises a resin.

12. The process of claim 1, wherein the solid support comprises a microporous polystyrene resin, a microporous polyethylene glycol resin, and/or a microporous co-polymer resin.

* * * * *

SEQUENCE LISTING

```
<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Fmoc

<400> SEQUENCE: 1

Ala Leu Phe Ala Leu Phe Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 2

Leu Tyr Arg Ala Gly
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3

Val Gln Ala Ala Ile Asp Tyr Ile Asn Gly
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 4

Gly Cys Cys Ser Leu Pro Pro Cys Ala Leu Asn Asn Pro Asp Tyr Cys
1               5                   10                  15
```

-continued

```
<210> SEQ ID NO 5
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 5

Pro Val Asn Ile Ile Gly Arg Asn Leu Leu Thr Gln Ile Gly Cys Thr
1               5                   10                  15

Leu Asn Phe

<210> SEQ ID NO 6
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg
            20                  25

<210> SEQ ID NO 7
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Thz

<400> SEQUENCE: 7

Ala Phe Ile Gln Ser Leu Lys Asp Asp Pro Ser
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 8

Cys Ser Ala Asn Leu Leu Ala Glu Ala Lys Lys Leu Asn Asp Ala Gln
1               5                   10                  15

Ala Pro Lys

<210> SEQ ID NO 9
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Fmoc

<400> SEQUENCE: 9

Val Asp Asn Lys Phe Asn Lys Glu Gln Gln Asn Ala Phe Tyr Glu Ile
1               5                   10                  15
```

Leu His Leu Pro Asn Leu Asn Glu Glu Gln Arg
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Boc
<220> FEATURE:
<221> NAME/KEY: misc_feature
<222> LOCATION: (33)..(33)
<223> OTHER INFORMATION: Xaa can be any naturally occurring amino acid

<400> SEQUENCE: 10

Gly Gly Gly Gly Gly Val Asp Asn Lys Phe Asn Lys Glu Gln Gln Asn
1               5                   10                  15

Ala Phe Tyr Glu Ile Leu His Leu Pro Asn Leu Asn Glu Glu Gln Arg
            20                  25                  30

Xaa

<210> SEQ ID NO 11
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Fmoc and Thz

<400> SEQUENCE: 11

Ala Phe Ile Gln Ser Leu Lys Asp Asp Pro Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Boc and Thz
<220> FEATURE:
<221> NAME/KEY: misc_feature
<222> LOCATION: (12)..(12)
<223> OTHER INFORMATION: Xaa can be any naturally occurring amino acid

<400> SEQUENCE: 12

Ala Phe Ile Gln Ser Leu Lys Asp Asp Pro Ser Xaa
1               5                   10

<210> SEQ ID NO 13
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Fmoc

```
<400> SEQUENCE: 13

Cys Ser Ala Asn Leu Leu Ala Glu Ala Lys Lys Leu Asn Asp Ala Gln
1               5                   10                  15

Ala Pro Lys

<210> SEQ ID NO 14
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Boc

<400> SEQUENCE: 14

Cys Ser Ala Asn Leu Leu Ala Glu Ala Lys Lys Leu Asn Asp Ala Gln
1               5                   10                  15

Ala Pro Lys

<210> SEQ ID NO 15
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 15

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Cys Ala Phe Ile Gln
            20                  25                  30

Ser Leu Lys Asp Asp Pro Ser
        35

<210> SEQ ID NO 16
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 16

Ala Gly Gln Gly Gly Tyr Gly Gly Leu Gly Ser Gln Gly Thr Ser Gly
1               5                   10                  15

Arg Gly Gly Leu Gly Gly Gln Gly
            20

<210> SEQ ID NO 17
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 17

Gly Gly Gly Gly Gly Ala Arg Leu Leu Arg Leu
1               5                   10

<210> SEQ ID NO 18
<211> LENGTH: 7
<212> TYPE: PRT
<213> ORGANISM: Artificial Sequence
```

```
<220> FEATURE:
<223> OTHER INFORMATION: Synthetic Polypeptide

<400> SEQUENCE: 18

Ala Leu Phe Ala Leu Phe Ala
1               5
```